(12) United States Patent
Sachdeva et al.

(10) Patent No.: US 7,296,996 B2
(45) Date of Patent: Nov. 20, 2007

(54) VIRTUAL BRACKET PLACEMENT AND EVALUATION

(75) Inventors: Rohit Sachdeva, Plano, TX (US); Peer Sporbert, Berlin (DE); Stephan Maetzel, Berlin (DE); Hans Imgrund, Berlin (DE); Claudia Strauss, Berlin (DE); Phillip Getto, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 484 days.

(21) Appl. No.: 10/791,440

(22) Filed: Mar. 2, 2004

(65) Prior Publication Data

US 2004/0214128 A1    Oct. 28, 2004

Related U.S. Application Data

(63) Continuation-in-part of application No. 10/684,252, filed on Oct. 9, 2003, which is a continuation of application No. 09/834,412, filed on Apr. 13, 2001, now Pat. No. 6,632,089, which is a continuation-in-part of application No. 09/560,640, filed on Apr. 28, 2000, now abandoned, which is a continuation-in-part of application No. 09/451,609, filed on Nov. 30, 1999, now Pat. No. 6,250,918, and a continuation-in-part of application No. 09/560,130, filed on Apr. 28, 2000, now Pat. No. 6,736,638.

(51) Int. Cl.
*A61C 7/00* (2006.01)
(52) U.S. Cl. .................................... 433/24
(58) Field of Classification Search ................. 433/24, 433/215, 223
See application file for complete search history.

(56) References Cited

U.S. PATENT DOCUMENTS

| | | | | |
|---|---|---|---|---|
| 3,332,150 A | * | 7/1967 | Mumaw | 433/24 |
| 5,011,405 A | * | 4/1991 | Lemchen | 433/24 |
| 5,431,562 A | * | 7/1995 | Andreiko et al. | 433/24 |
| 5,879,158 A | * | 3/1999 | Doyle et al. | 433/24 |
| 5,975,893 A | * | 11/1999 | Chishti et al. | 433/6 |
| 6,068,482 A | * | 5/2000 | Snow | 433/223 |
| 6,089,868 A | * | 7/2000 | Jordan et al. | 433/215 |
| 6,244,861 B1 | * | 6/2001 | Andreiko et al. | 433/3 |
| 6,334,772 B1 | * | 1/2002 | Taub et al. | 433/24 |
| 6,406,292 B1 | * | 6/2002 | Chishti et al. | 433/24 |
| 6,450,807 B1 | * | 9/2002 | Chishti et al. | 433/24 |
| 6,471,511 B1 | * | 10/2002 | Chishti et al. | 433/24 |

\* cited by examiner

*Primary Examiner*—Melba Bumgarner
(74) *Attorney, Agent, or Firm*—McDonnell Boehnen Hulbert & Berghoff LLP

(57) ABSTRACT

A method and apparatus for facilitating placement and evaluation of virtual appliances on virtual teeth of an orthodontic patient are described. Positioning references comprising bracket height, occlusal plane, or any arbitrary plane are provided to facilitate desired placement of virtual appliances on virtual teeth model. The process can be applied with any dentition state of a patient such as malocclusion, target state from treatment, or intermediate monitored state during the course of a treatment. An unified workstation for treatment planning provides the computer software tools for verification, simulation and evaluation of the virtual appliance placement. The process enables proper planning of treatment for an orthodontic patient suffering from malocclusion involving bonding of virtual brackets to the surface of the patient's virtual teeth with archwires placed in the slots of the brackets, so as to realize the desired results from the treatment in the most desired manner.

73 Claims, 20 Drawing Sheets

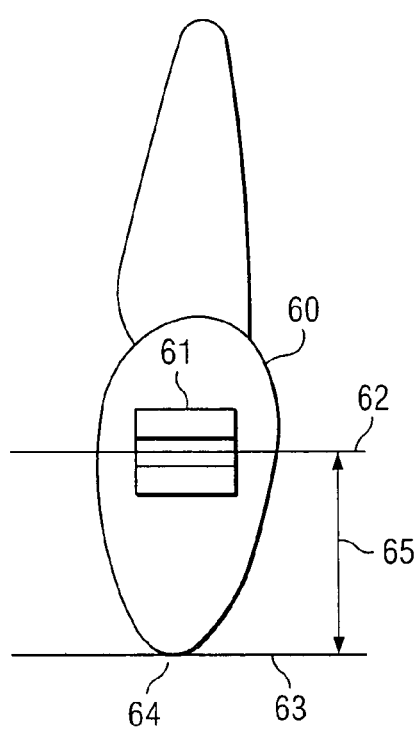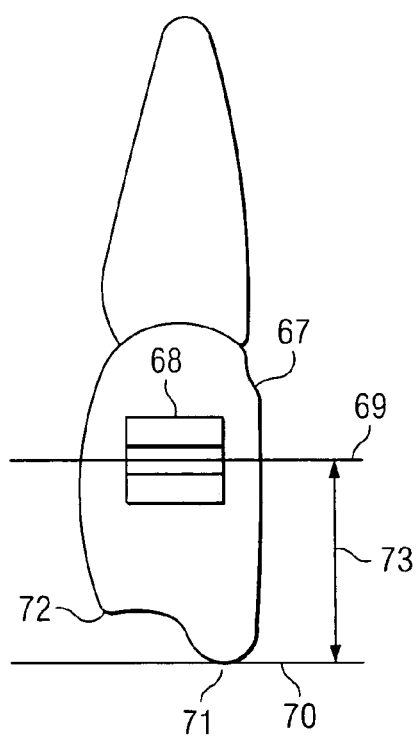
FIG. 2A         FIG. 2B
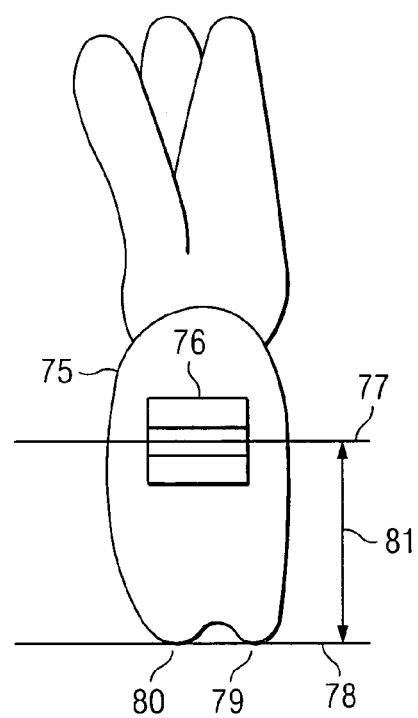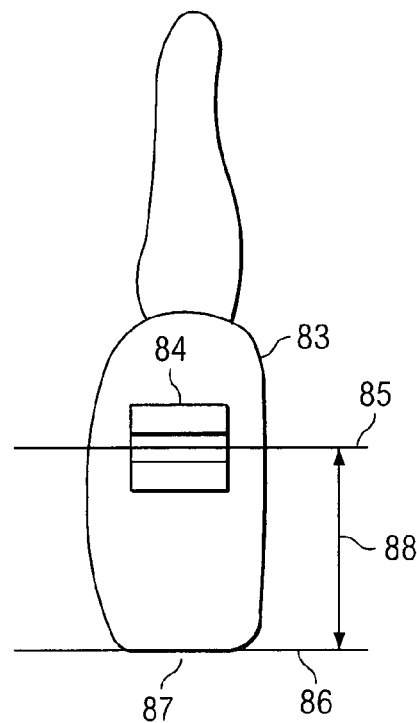
FIG. 2C         FIG. 2D

VIRTUAL BRACKET PLACEMENT AND EVALUATION

CROSS-REFERENCE TO RELATED APPLICATIONS

This application is a continuation-in-part application of the following U.S. patent applications:

Ser. No. 10/684,252 filed Oct. 9, 2003, pending, which is a continuation of Ser. No. 09/834,412 filed Apr. 13, 2001 now issued as U.S. Pat. No. 6,632,089, which is a continuation-in-part of Ser. No. 09/560,640 filed Apr. 28, 2000 now abandoned, pending, which is a continuation in part of Ser. No. 09/451,609 filed Nov. 30, 1999 now issued as U. S. Pat. No. 6,250,918, and Ser. No. 09/560,130 filed Apr. 28, 2000 now U.S. Pat. No.6,736,638, pending. The entire contents of each of the above-referenced patent applications are incorporated by reference herein.

BACKGROUND OF THE INVENTION

A. Field of the Invention

This invention relates generally to the field of computer-interactive methods for diagnosis, care and treatment planning, therapeutics and treatment monitoring in the medical arena, including orthodontics and in particular to a computerized and interactive method of facilitating placement and evaluation of orthodontic appliances for treatment of a patient. In the method, the patient's teeth are represented in a computer as three-dimensional virtual objects. The orthodontist may simulate various types of appliances, their placements and tooth movement, analyze the simulation results, and thereby explore possible treatment options that would produce the desired results.

B. Description of Related Art

In orthodontics, a patient suffering from a malocclusion is typically treated by bonding brackets to the surface of the patient's teeth and placing archwires in the slots of the brackets. The bracket-archwire interaction governs forces applied to the teeth and defines the direction of tooth movement. Therefore, the placement of brackets on the patient's teeth plays a crucial role in the outcome of the treatment. When the brackets are placed properly, and the archwire bent accordingly, the desired results from the treatment are achieved in the most efficient manner; otherwise, the treatment could last much longer.

Typically, orthodontists utilize their expertise to first determine a three-dimensional mental image of the patient's current physical orthodontic structure and a three-dimensional mental image of a desired physical orthodontic structure for the patient, which may be assisted through the use of x-rays and/or models. Based on these mental images, the orthodontist further relies on his or her expertise to place, for example, the brackets and/or the O-rings on the teeth. Unfortunately, in the oral environment, it is impossible, using human sight, to accurately develop a three-dimensional mental image of an orthodontic structure due to the limitations of human site and the physical structure of a human mouth. Further it is humanly impossible to determine an ideal bracket location to achieve the desired orthodontic structure based on mental images. It is also extremely difficult to manually place brackets in the estimated ideal location, to control bonding agent thickness, ligation forces, manufacturing tolerances, and biological changes.

Alternatively, orthodontists have the possibility of taking plaster models of the upper and lower jaws, cutting the model into single tooth models and sticking these tooth models into a wax bed, lining them up in the desired position, the so-called set-up. The next step is to bond a bracket at every tooth model. This would tell the orthodontist the geometry of the wire to run through the bracket slots to receive exactly this result. The next step involves the transfer of the bracket position to the original malocclusion model. Such physical modeling would provide only very limited treatment simulation capability, and could be time consuming and expensive.

Additionally, orthodontists may utilize commercially available bracket height-measuring gauges or a set of dividers, such as for example marketed by Ormco corporation, 1717 West Collins Avenue, Orange, Calif. 92867, USA, to guide them in determining and marking the bracket placement positions on teeth. Such gauges can be used in conjunction with a physical model of the patient's teeth as well as with the patient's real teeth. However, when the patient's teeth are crooked and hard to measure, e.g., with perverted axial inclination, usefulness of such gauges could be limited; and may not yield the desired accuracy in placing the brackets. Furthermore, such physical gauges are generally limited in capability in that they are intended for measurements solely from good cusp tips. Also consistency in measurements is critical, which may be difficult to achieve in manual measurements. The gauge positioning is likely to influence the measurement.

As described, the practice of orthodontic is very much an art, relying on the expert opinion and judgment of the orthodontist. In an effort to shift the practice of the orthodontic from an art to a science, many innovations have been developed. For example, U.S. Pat. No. 5,518,397 issued to Andreiko, et. al, provides a method of forming an orthodontic brace. Such a method includes obtaining a model of the teeth of a patient's mouth and a prescription of desired positioning of such teeth. The two-dimensional contour of the teeth of the patient's mouth is determined from the model. Calculations of the contour and the desired positioning of the patient's teeth are then made to determine the geometry (e.g., grooves or slots to be provided in the brackets) are created. Custom brackets including a special geometry have been created for receiving an arch wire to form an orthodontic brace system. Such geometry is intended to provide for the disposition of the arched wire on the bracket in a progressive curvature of a horizontal plane and a substantially linear configuration in a vertical plane. The geometry of the bracket is altered, (e.g., by cutting grooves into the bracket at individual positions and angles and with particular depth) and in accordance with such calculations of the geometry of the patient's teeth. In such a system, the brackets are customized to provide three-dimensional movement of the teeth once the wire, which has a two-dimensional shape, (i.e., linear shape in the vertical plane and curvature in the horizontal plane) is applied to the brackets.

To assist in the accurate placement of brackets on a tooth, a jig may be utilized. One such jig is disclosed in U.S. Pat. No. 5,368,478 issued to Andreiko, et. al which provides a method for forming jigs for custom placement of orthodontic appliances on teeth. In general, the '478 patent teaches that each jig is provided with a surface conforming to the contour of the tooth to which they are to be mounted. Another surface of the jig engages the bracket to hold it in the proper position and orientation for mounting to the tooth and spaced in relation to the contour surface to precisely locate the jig on the tooth. The jigs are particularly useful in positioning brackets of custom appliances desired to the individual anatomy of the patient and requiring custom positions of the brackets on the teeth. While the '478 patent discloses a method for forming a jig, such jig utilization still keeps the bracket as the focal point of the orthodontic treatment and provides no feedback mechanism regarding actual placement of the bracket. Further, the '478 patent does not allow for variables associated with tooth movement such as static, dynamic, or psychosocial mechanical and/or biological changes.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

U.S. Pat. No. 5,879,158 to Doyle et al. describes an orthodontic bracketing system and method. To start with, from a negative impression of a patient's teeth, a positive hard duplicate pattern such as a stone model of the teeth is made. A digitized three dimensional coded image of the teeth is then generated by means of a coordinate measuring machine or by laser scanning. The central axis of each tooth is then displayed in an exploded image of the set of teeth and each tooth is moved in virtual space to a desired position and orientation using torque, tip and angulation values as well as in/out position information provided by the selected orthodontic bracket system. The optimum position of each tooth-mounted orthodontic appliance bracket and its attachment point to its associated tooth for moving the tooth to a desired orientation and position is then determined using the digitized coded images of each tooth including its central axis in its initial and final desired position and orientation. Using this bracket attachment information for each tooth, the shape and contour of a bracket attachment jig is determined for each tooth and this information in digital form is used to fabricate a plurality of such jigs under computer control such as by using a computer numeric control (CNC) milling machine for attaching an off-the-shelf, conventional orthodontic bracket to each tooth. Conventional archwires attached to the upper and lower optimally positioned brackets urge each tooth to its respective desired position and orientation with minimal subsequent manipulation and adjustment of the archwires by the orthodontist.

U.S. Pat. No. 6,334,772 to Taub et al. describes a method, system and device for positioning and fixing an orthodontic element on a surface of a tooth. The positioning of the element on a tooth is accomplished by: bringing the element into proximity of the tooth while continuously capturing an image of at least the tooth or of the element, and an image of both, once the tooth and the element are proximal to one another; transmitting the image or its representation to a display for displaying a real-life image of the captured image or representation together with indicators providing guidance information on intended position of the orthodontic element on the tooth's surface; positioning the element on a tooth's surface according to the indicators such that the element's position coincides with the intended position; and fixing the element onto the tooth.

U.S. Patent Application Publication No. 2003/0143509 A1 to Kopelman et al. describes a method and system for providing information for correct placement of one or more brackets on one or more corresponding teeth according to a predetermined treatment scheme. A virtual representation of a three-dimensional teeth arrangement of one or both jaws of the individual with brackets placed on said teeth is obtained, wherein the position and orientation of the brackets on said teeth being designed so as to achieve a desired treatment outcome. The virtual representation is processed to generate an output data, the output data driving a display, such as a computer monitor or a printed "hard-copy", to display an image of at least one tooth with a bracket thereon, the displayed image having three-dimensional qualities indicative of said at least one tooth as viewed from a defined viewpoint. The invention can be applied to the placement of brackets onto the buccal side of the teeth as well as onto the lingual side of the teeth.

Unfortunately, the current innovations to change the practice of orthodontic from an art to a science have only made limited progress. Placement of each bracket on a corresponding tooth is critical. A misplacement of a bracket by a small amount (e.g., an error vector having a magnitude of a millimeter or less and an angle of a few degrees or less) can cause a different force system (i.e., magnitude of movement and direction of movement) than the desired force system to be applied to the teeth. As such, the tooth will not be repositioned to the desired location.

Therefore, to further enhance the accuracy of orthodontic treatment a need exists for enabling the practitioners by facilitating modeling of accurate placement of orthodontic appliances and simulating their impact on teeth movement in conjunction with matching archwire configurations.

SUMMARY OF THE INVENTION

The invention provides user selectable appliance placement references for enabling the practitioner or the user in placing virtual appliances such as virtual brackets on virtual teeth model of a patient, and in evaluating their effectiveness in realizing the desired goals of the treatment. In a preferred embodiment of the invention, an appliance height reference is provided for facilitating placement of the virtual appliances on a three-dimensional model of a patient's teeth. In a preferred aspect of the invention, the appliance height reference is implemented as a bracket height reference for placing virtual brackets on virtual teeth of a patient. The user selects a value for placing the virtual bracket on the virtual tooth at the desired bracket height from the reference options available on the unified workstation for orthodontic treatment planning, described later on in greater detail, and the unified workstation places and displays the virtual bracket on the virtual tooth at or near the selected height depending upon the tooth surface geometry and texture for suitably accepting the bracket. Alternatively, the user can specify the desired or customized bracket height reference value for placing the virtual bracket on the virtual tooth. The bracket height reference is similar in functionality to the bracket height measured from a bracket height-measuring gauge; but provides much improved accuracy and consistency in the height measurements over the bracket height-measuring gauge. Additionally, meaningful height measurements for crooked or deformed teeth that are very difficult to realize with the bracket height-measuring gauge can easily be made with the bracket height reference of the present invention.

In another embodiment of the invention, an user selectable occlusal plane reference is provided for facilitating placement of virtual appliances such as virtual brackets on three-dimensional model of a patient's teeth and evaluation thereafter of the effectiveness of the underlying treatment. The occlusal plane reference is derived from the occlusal plane. There are several definitions of the occlusal plane possible and implemented according to the present invention, one of which is that it is a compound curved surface or a curved surface that touches the incisal edges of the incisors and the cusp tips of the occluding surfaces of the posterior teeth. In one embodiment of the invention, the occlusal plane is approximated by a flat plane based on specific reference points within the dental arches. In one embodiment of the invention, the occlusal plane is derived from the cusp tips. In yet another embodiment, the occlusal plane reference is derived from marginal ridges. In yet another embodiment, the occlusal plane reference is derived arbitrarily. The occlusal plane reference can be used either as a lower occlusal plane reference to facilitate placement of the virtual brackets on the three-dimensional model of the patient's lower teeth, an upper occlusal plane reference to facilitate placement of the virtual brackets on the three-dimensional model of the patient's upper teeth, or simultaneously as a lower occlusal plane reference and an upper occlusal plane reference to facilitate placement of the virtual brackets on the three-dimensional model of the patient's lower and upper teeth. Furthermore, the occlusal plane reference can be used as a complete unit for all virtual teeth or it can be used in user defined segments for individual or groups of virtual teeth. Once selected by the user, the occlusal plane reference is superimposed on the virtual teeth by the treatment planning unified workstation; and a capability is provided for the user to move it to a desired position for placement of the virtual appliances or brackets on the virtual teeth.

In yet another embodiment of the invention, an user selectable arbitrary plane reference is provided for facilitating placement of virtual appliances such as virtual brackets on three-dimensional model of a patient's teeth. The arbitrary plane reference is defined by the user, and can be used in a manner similar to the occlusal plane reference, i.e., for placing virtual brackets on the three-dimensional model of the lower teeth, the upper teeth, or all teeth; and it can be used as a complete unit covering all virtual teeth or in user defined segments covering individual or groups of virtual teeth. Like the occlusal plane reference, once selected by the user, the arbitrary plane reference is superimposed on the virtual teeth by the treatment planning unified workstation; and a capability is provided for the user to move it to a desired position for placement of the virtual appliances or brackets on the virtual teeth.

In a first aspect of the invention, the appliance placement references of the present invention can be used in conjunction with a patient's malocclusion state or a treatment target state. In a second aspect of the invention, the appliance placement references of the present invention can be used in conjunction with a patient's intermediate state monitored during the ongoing treatment of the patient.

The appliance placement references are provided in an apparatus or workstation for treatment planning for an orthodontic patient. The apparatus can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition and to develop and specify a target or desired stage. The apparatus provides for simulation of tooth movement between current and target stages.

In its broader aspects, the treatment planning apparatus comprises a workstation having a processing unit and a display, and a memory storing a virtual, complete three-dimensional model representing the dentition of a patient. The virtual three-dimensional model can be obtained from one of several possible sources; including from a scanning of the dentition. The apparatus further includes software executable by the processing unit that accesses the model and displays the model on the display of the workstation. The software further includes navigation tools, e.g., typed commands, icons and/or graphical devices superimposed on the displayed model, that enables a user to manipulate the model on the display and simulate the movement of at least one tooth in the model relative to other teeth in the model in three-dimensional space, and quantify the amount of movement precisely. This simulation can be used, for example, to simulate the bracket placement on virtual teeth of the patient.

The development of a unique target situation for the patient has utility in a variety of different orthodontic appliances, including an approach based on off-the-shelf or generic brackets and a custom orthodontic archwire. The scope of the invention is sufficient to encompass other types of appliances, such as an approach based on customized brackets, retainers, etc. In a bracket embodiment, the memory contains a library of virtual, three-dimensional orthodontic brackets. The software permits a user to access the virtual brackets through a suitable screen display, and place the virtual brackets on the virtual model of the dentition of the patient. This bracket bonding position can be customized on a tooth by tooth basis to suit individual patient anatomy. Because the tooth models, brackets and archwire are individual objects, and stored as such in memory, the treatment planning apparatus can simultaneously display the virtual brackets, the archwire and the virtual model of the dentition, or some lesser combination, such as just the brackets, just the dentition, or the brackets and the archwire but not the teeth. The same holds true with other appliance systems.

The virtual model of teeth comprises a set of virtual, individual three-dimensional objects, such as the tooth objects, and other virtual objects of associated anatomical structures, e.g., gums, roots and bone. When the teeth are separated from each other and from the gums, they can be individually manipulated. Thus, the tooth objects can be individually selected and moved relative to other teeth in the set of virtual tooth objects. This feature permits individual, customized tooth positioning on a tooth by tooth basis. These positioning can be in terms or angular rotation about three axis, or translation in transverse, sagittal or coronal planes. Additionally, various measurement features are provided for quantifying the amount of movement.

One of the primary tools in the treatment planning apparatus is the selection and customization of a desired or target archform. Again, because the teeth are individual tooth objects, they can be moved independently of each other to define an ideal arch. This development of the target archform could be calculated using interpolation or cubic spline algorithms. Alternatively, it can be customized by the user specifying a type of archform (e.g, Roth), and the tooth are moved onto that archform or some modification of that archform. The archform can be shaped to meet the anatomical constraints of the patient. After the initial archform is designed, the user can again position the teeth on the archform as they deem appropriate on a tooth by tooth basis.

The treatment planning software thus enables the movement of the virtual tooth objects onto an archform which may represent, at least in part, a proposed treatment objective for the patient.

Numerous other features are possible with the treatment planning software, including movement of the teeth with respect to the other teeth in the archform, changing the position of the virtual brackets and the teeth with respect to each other, or opposing teeth with respect to the selected archform. Custom archwire bends can be simulated to provide additional corrections. Bonding corrections at the bracket-tooth interface are also possible.

The treatment planning apparatus obtains and stores a three-dimensional virtual model of teeth representing the dentition of the patient in a current or observed situation. The virtual model is displayed on the display. The method further includes the step of moving the position of teeth in the virtual model relative to each other so as to place the teeth of the virtual model into a target situation and displaying the virtual model with the teeth moved to the target situation to the user. Parameters for an orthodontic appliance to move the patient's teeth from the current situation to the target situation can be derived from the virtual model and the target situation. For example, if virtual brackets are placed on the teeth, their location in the target situation can dictate the design of an archwire to move the teeth to the target situation.

In a preferred embodiment, the method of placing brackets on three-dimensional model of the patient's teeth using bracket placement references includes the step of providing displays on the screen display enabling a user of the workstation to operate the user interface so as to place virtual three-dimensional objects representing orthodontic appliances, e.g., brackets, onto the surface of teeth in the virtual model. A library of the virtual brackets can be stored in memory and a landmarking procedure used to place the brackets on the teeth at the desired location. Anatomical considerations may dictate movement of the brackets from their originally selected position to a new position. Accordingly, the software provides navigational tools enabling a user to change the position of the brackets relative to the teeth.

The treatment planning system is based on individual tooth objects which can be moved to any position in three dimensional space. They can be moved in several ways—by direct user specified movement, and by adding an object comprising an orthodontic appliance and changing the configuration of the appliance to cause the teeth to move. For example brackets can be virtually bonded to the teeth and the position of the brackets changed in three dimensions to move the teeth. Alternatively, an archwire shape can be defined which fits into the slots in the brackets. Movement and shape of the archwire can be simulated and evaluated in conjunction with the placement of the brackets, resulting in a simulation of tooth movement so as to select the most desired bracket configuration. The desired bracket configuration can be printed from the treatment planning workstation and can be used by the practitioner as a visual guide while placing the real appliances or brackets on the actual teeth of a patient.

The treatment planning software includes features enabling more accurate diagnosis. For one thing, the virtual model of the dentition can be manipulated in three dimensions at will, resulting in complete visual assessment of the model. Measurement tools are also provided by which the orthodontist can determine the distance between any two points on the model. This allows the user to quantify the patient's morphology both at initial and at target stages or states. Thus, treatment progress, proposed changes in appliance design, or tooth movement can be quantified precisely. By measuring the differences and changes in morphology during the care cycle, the orthodontist can quickly and accurately assess patient treatment. Changes in treatment can be made early on. The result is shorter treatment times (and the ability for the orthodontist to service more patients per year).

The treatment planning system incorporates virtual objects comprising orthodontic appliances that may be used to treat the patient. The treatment planning system provides for design of complete appliance systems and simulation of various appliance designs and associated tooth movement, in a computer-interactive fashion.

These and many other features of the presently preferred embodiment of the bracket placement and evaluation apparatus and method are set forth below.

BRIEF DESCRIPTION OF THE DRAWINGS

FIGS. 2(a)-2(d) illustrate selection of the contact points on teeth and corresponding bracket height references for various categories of teeth according to the present invention. FIG. 2(a) provides the illustration for the canine category of teeth, FIG. 2(b) for the pre-molar category of teeth, FIG. 2(c) for the molar category of teeth, and FIG. 2(d) for the incisor category of teeth.

FIG. 7 also illustrates icons for selecting a reference, e.g. bracket height reference, occlusal plane reference, or arbitrary plane reference, for placing virtual appliances on the patient's virtual teeth according to the present invention.

DETAILED DESCRIPTION OF PREFERRED EMBODIMENT

The present invention provides a method and apparatus for facilitating placement and evaluation of virtual appliances, such as virtual brackets, on virtual teeth of an orthodontic patient. The invention provides user selectable positioning references to facilitate initial automatic placement of virtual appliances on virtual teeth model. The appliance placement references can be used by a practitioner or a user in accordance with the practitioner's preferences and enable taking into account anatomical properties and features of patient's teeth while planning treatment. Once the virtual appliances are placed on the virtual teeth using the placement references a easy to use capability is provided for making adjustment of the virtual appliance placement. This invention enables proper planning of treatment for orthodontic patients. For an orthodontic patient suffering from a malocclusion treated by bonding brackets to the surface of the patient's teeth and placing archwires in the slots of the brackets, it is very important that the brackets are placed properly, and the archwires configured accordingly, so as to realize the desired results from the treatment in the most efficient manner.

Figure 1:
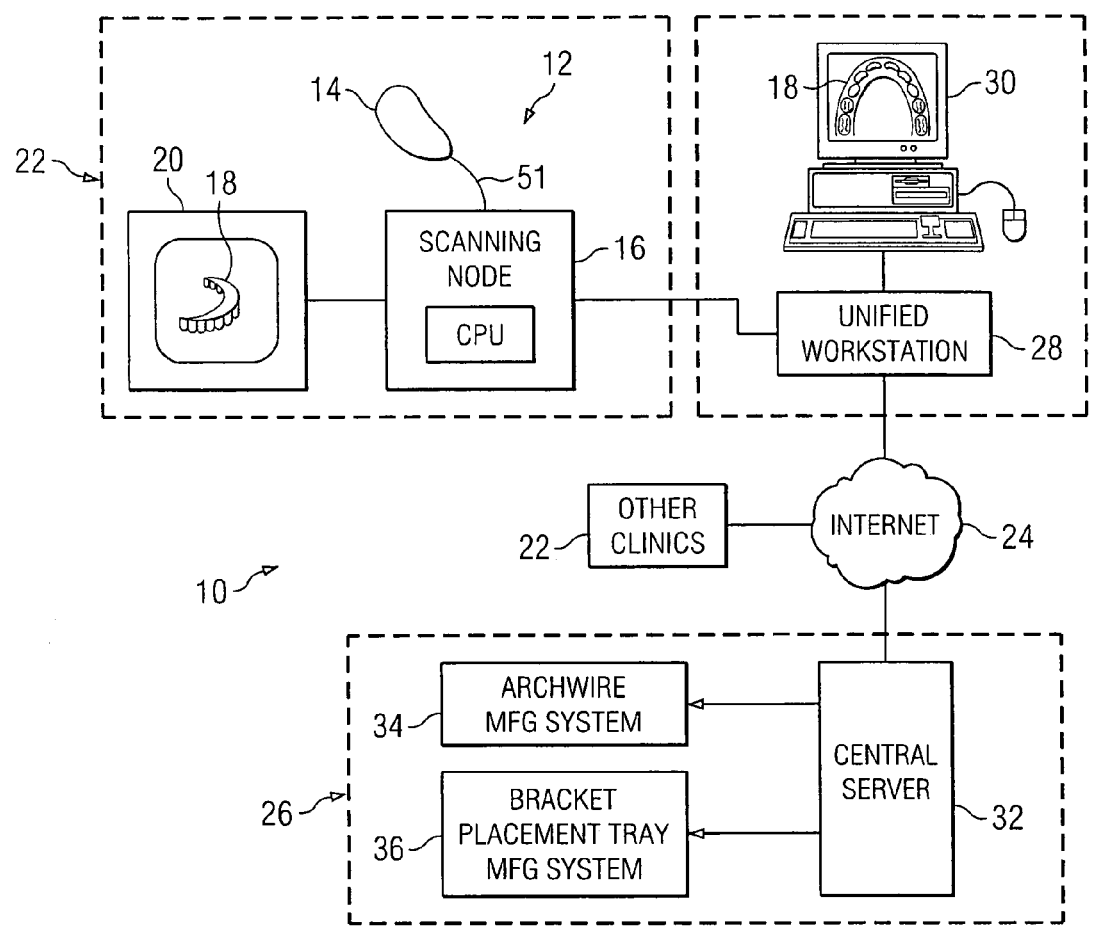
FIG. 1 illustrates an orthodontic care system that incorporates a unified workstation for treatment planning useful in the present invention.

The present invention is best practiced through a unified workstation 28 incorporated into orthodontic care system 10 illustrated in FIG. 1. The workstation 28 includes a general-purpose computer system having a processor (CPU) and a user interface, including screen display 30, mouse and keyboard. The orthodontic care system 10 further incorporates a scanner system 12. The scanner system 12 includes a hand-held scanner 14 that is used by the orthodontist to acquire three-dimensional information of the dentition and associated anatomical structures of a patient. The images are processed in a scanning node or workstation 16 having a central processing unit, such as a general-purpose computer. The scanning node 16, either alone or in combination with workstation 28, generates a three-dimensional virtual computer model 18 of the dentition. The virtual teeth model provides the orthodontist and the treatment planning software with a base of information to plan treatment for the patient. The model 18 is displayed to the user on a monitor 20 connected to the scanning node 16, and is also made available at monitor 30 of workstation 28. In order to assist in treatment planning, the three dimensional model is created by separating the virtual teeth from the surfaces representing the gums and other anatomical structure, and presenting the crowns of the teeth to the orthodontist or the user. Alternatively, roots of teeth from a template of three-dimensional template roots can be associated with each tooth. The roots could also come wholly or partially from 2-D sources such as X-rays of the roots, or from a 3-D source such as ultrasound or CAT scanner. The tooth separation process allows individual teeth to be moved independently in three dimensions on the computer in an interactive, user-specified manner, since they are individual three-dimensional objects.

The orthodontic treatment planning can work with any three-dimensional tooth objects, regardless of their source. In the illustrated embodiment, the three dimensional objects comprise tooth objects obtained from a scanning of the dentition of the patient. The manner of developing these three-dimensional tooth objects is described at length in the patent application of Rudger Rubbert et al. filed Apr. 13, 2001, entitled SCANNING SYSTEM AND CALIBRATION METHOD FOR CAPTURING PRECISE THREE-DIMENSIONAL INFORMATION OF OBJECTS Ser. No. 09/834,593, the contents of which are incorporated by reference herein. Other possibilities are 3-D models obtained from CAT scans, laser scans, ultrasound, 3-D photogrammetry of models, or other type of scanning taken either in-vivo or from a plaster model, or some combination of these techniques.

The workstation 28 stores other digital data representing patient craniofacial image information of the patient obtained through other devices not shown in FIG. 1. In a representative and non-limiting example of the data sets, the data set could be a set of two dimensional color photographs of the face and head of the patient obtained via a color digital camera. The workstation 28 may also store other sets of digital image data, including digitized X-ray photographs, MRI or ultrasound images, CT scanner etc., from other imaging devices not shown in FIG. 1. The other imaging devices need not be located at the situs of workstation system 28. Rather, the imaging of the patient with one or other imaging devices could be performed in a remotely located clinic or hospital, in which case the image data is obtained by the workstation 28 over the Internet 24 or some other communications medium and stored in the memory of or accessible to workstation 28.

The workstation 28 further includes a set of computer instructions stored on a machine-readable storage medium. The instructions may be stored in the memory, not shown in FIG. 1, accessible to the workstation 28. The machine-readable medium storing the instructions may alternatively be a hard disk memory for the workstation 28, external memory devices, or may be resident on a file server on a network connected to the workstation, the details of which are not important. The set of instructions, described in more detail below, comprise instructions for causing the workstation 28 to perform several functions related to the generation and use of the virtual patient model in diagnostics, therapeutics and treatment planning.

These functions include a function of automatically, and/or with the aid of operator interaction via the user interface, superimposing different sets of digital data so as to provide a composite, combined digital three-dimensional representation of the craniofacial anatomical structures in a common three-dimensional coordinate system. Preferably, one of the sets of data includes photographic image data of the patient's face, teeth and head, obtained with a color digital camera. The other set of data, besides intra-oral 3D scan data obtained from the hand-held scanner 14, could be CT scan data, X-Ray data, MRI, etc. In the example of FIG. 1, the hand-held scanner 14 acquires a series of images containing 3D information and this information is used to generate a 3D virtual teeth model in the scanning node 12, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model in accordance with the teachings of the patent application of Rohit Sachdeva et al. filed on May 2, 2003, entitled UNIFIED WORKSTATION FOR VIRTUAL CRANIOFACIAL DIAGNOSIS, TREATMENT PLANNING AND THERAPEUTICS, Ser. No. 10/429,123, the contents of which are incorporated by reference herein. These data sets are superimposed with each other, with appropriate scaling as necessary to place them in registry with each other and at the same scale. The resulting representation can be stored as 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions of the workstation 28 further include computer-aided design (CAD)-type software tools to display the virtual model to the user and provide the user with tools for viewing and studying the model. Preferably, the model is capable of being viewed in any orientation. Tools are provided for showing slices or sections through the model at arbitrary, user defined planes. Alternatively, the composite digital representation may be printed out on a printer or otherwise provided to the user in a visual form.

The treatment planning software includes features to enable the orthodontist or the user to manipulate the model 18 to plan treatment for the patient. The treatment planning method provides a wealth of viewing, measuring, and simulation tools by which the orthodontist can plan treatment for any given patient. The workstation environment provides a powerful system for purposes of diagnosis, treatment planning and delivery of therapeutics. For example, from the location and position of individual anatomical structures e.g., individual tooth positions and orientation, shape of arch and position of upper and lower arches relative to each other, it is possible to automatically back solve for or derive the jaw, tooth, bone and/or soft tissue corrections that must be applied to the patient's initial, pre-treatment position to provide the desired result. This leads directly to a patient treatment plan.

The simulation tools comprise user-friendly and intuitive icons that are activated by a mouse or keyboard on the user interface of the workstation 28. When these icons are activated, the software instruction provide pop-up menu, or other types screens that enable a practitioner or a user to navigate through particular tasks to highlight and select individual anatomical features, change their positions relative to other structures, and simulate movement of the teeth, jaws (chewing or occlusion), etc. Examples of the types of navigational tools, icons and treatment planning tools for a computer user interface that may be useful in this process are described in the patent application of Rudger Rubbert et al., Ser. No. 10/280,758 filed Oct. 24, 2002, entitled "INTERACTIVE ORTHODONTIC CARE SYSTEM BASED ON INTRA-ORAL SCANNING OF TEETH," the contents of which are incorporated by reference herein.

The virtual patient model, or some portion thereof, such as data describing a three-dimensional model of the teeth in initial and target or treatment positions, is useful information for planning treatment of the patient. The position of the teeth in the initial and desired positions can be used to evaluate the suitability of virtual appliance placement on virtual teeth of the patient.

Using the workstation 28, the progress of treatment can be monitored by periodically obtaining updated three-dimensional information regarding the progress of treatment of the patient, such as by obtaining updated scans of the patient and comparison of the resulting 3D model with the original 3D model of the patient prior to initiation of treatment.

The illustrated orthodontic care system consists of a plurality of orthodontic clinics 22 which are linked via the Internet or other suitable communications medium 24 (such as the public switched telephone network, cable network, etc.) to a precision appliance service center 26. Each clinic 22 has the scanning node 12 and may have the work station 28 or connect to the workstation 28 via internet or other means.

When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22.

As shown in FIG. 1, the precision appliance service center 26 includes a central server 32, an archwire manufacturing system 34 and a bracket placement manufacturing system 36. These details are not particularly important to the present invention and are therefor omitted from the present discussion for sake of brevity. For more details on these aspects of the illustrated orthodontic care system, the interested reader is directed to the previously mentioned patent application of Rudger Rubbert et al., filed Oct. 24, 2002, entitled INTER- ACTIVE ORTHODONTIC CARE SYSTEM BASED ON INTRA-ORAL SCANNING OF TEETH, Ser. No. 10/280,758.

In the illustrated embodiment, the treatment planning system also uses three-dimensional objects comprising virtual models of orthodontic appliances, such as brackets and orthodontic archwires. The bracket models can be obtained as CAD models from bracket manufacturers, or from a scanning of the brackets themselves. The unified workstation 28 stores a library of virtual brackets, the details of which are described in the patent application of Rohit Sachdeva et al. filed on May 1, 2002, entitled VIRTUAL BRACKET LIBRARY AND USES THEREOF IN ORTHODONTIC TREATMENT PLANNING, Ser. No. 10/137,523, and the corresponding published PCT application of OraMetrix, PCT publication no. WO 03/092529 A1, the contents of each of which are incorporated by reference herein. The wire models can be derived from the cross-sectional shape and length of the wire, and parameters as to the shape of an arch that the wire is representing (including loops). Obviously, in other types of orthodontic treatment scenarios where brackets are not used, other types of virtual three-dimensional objects may be used, such as retainers, Herbst appliances, etc.

Figure 2:
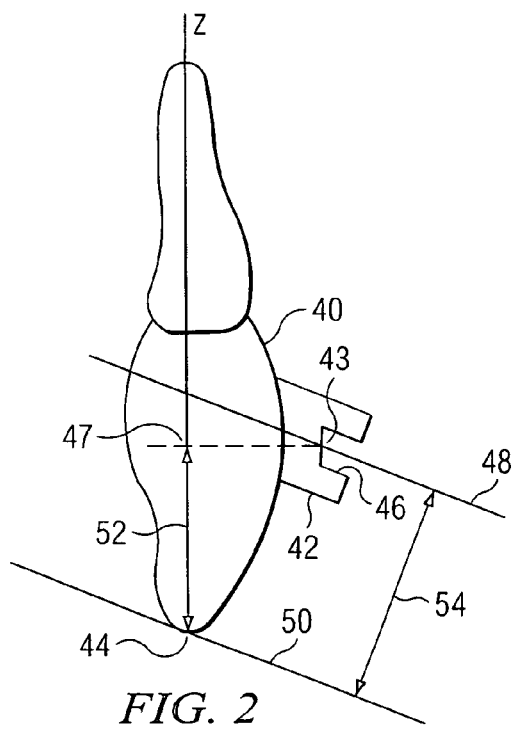
FIG. 2 illustration aids in describing one possible implementation to determine or calculate the bracket height reference for vertical positioning of a virtual bracket on a virtual tooth according to the preferred embodiment of the present invention.

The preferred embodiment of the invention provides user selectable appliance height as a reference to facilitate placement of virtual appliances on virtual teeth of a patient using a treatment planning workstation. In a preferred aspect of the invention, the appliance height reference is implemented as a bracket height reference for placing virtual brackets on virtual teeth of a patient. The user selects a value for placing the virtual bracket on the virtual tooth at the desired bracket height from the reference options available on the unified workstation 28 for orthodontic treatment planning and the unified workstation 28 places and displays the virtual bracket on the virtual tooth at or near the selected height depending upon the tooth surface geometry and texture for suitably accepting the bracket. Alternatively, the user can specify the desired or customized bracket height reference value for placing the virtual bracket on the virtual tooth. One skilled in the art would realize that there are numerous ways in which a virtual bracket positioning height or distance can be measured depending upon the starting point on the virtual tooth chosen for measuring the height or the distance and the route chosen for measuring the height or the distance between the starting point on the tooth and the center of the slot on the virtual bracket placed on the virtual tooth. Without loss of generality, one possible implementation to determine or calculate the bracket height reference for vertical positioning of a virtual bracket on a virtual tooth is described with the aid of illustration in FIG. 2 and as follows:

FIG. 2 shows a virtual tooth 40 having a virtual bracket 42 tentatively placed upon it at the location shown to start the process of determining the final placement of the virtual bracket as per the bracket height reference selected by the user. The virtual bracket 42 has the bracket slot 43 having the center point of the bracket-slot bottom located at point 46. The center point 46 is located at the bracket-slot bottom at the center of the width and length (not shown in FIG. 2) of the bracket slot. In this case, as shown in FIG. 2, the bracket height is defined as the perpendicular distance 54 between two parallel planes, namely the virtual bracket-slot-plane 48 and the virtual anchor plane 50. The bracket height 54 is measured along the vector perpendicular to both of these planes 48 and 50.

The virtual bracket-slot-plane 48 is defined by the bracket slot 43 for the selected virtual bracket 42 positioned on the surface of the virtual tooth 40 under consideration, and determined by the bracket slot 43 coordinates (not shown in FIG. 2) in mesial-distal and in-out directions including rotation values for torque and angulation which are built in the virtual bracket 42. The virtual bracket 42 to the tooth 40 relation is defined by a (minimal) three-point contact (not shown in FIG. 2) between the bracket 42 base and the tooth 40 surface in order to take into account the geometry and texture of the surface of the tooth for feasible placement of the virtual bracket thereon. The bracket-slot-plane 48 is placed at the bracket height distance 54 from the virtual anchor plane 50.

The virtual anchor plane 50 is parallel to bracket-slot-plane 48 and intersects (contains) a defined point 44. In general, this defined point 44 can be (a) the (labial) maxima on a occlusal tooth surface or (b) any other point at tooth feature, e.g. marginal ridges.

Without limiting the scope of the present invention, one description of the virtual bracket placement algorithm in accordance with the bracket height reference defined above is given in pseudo code as follows:

Let the virtual tooth 40 be oriented in a manner that the incisal edges are pointing in the z-direction of a global coordination system as shown in FIG. 2.

Define plane 48 such that it is perpendicular to the bottom of the slot 43 of the virtual bracket 42 and parallel to the flanks of the slot and divides the slot in two equal parts.

Define a starting position z, $z_0$=$bhr_z$, with the given virtual bracket height $bhr_z$ relative to maximum point 44 of the surface of the tooth 40 in the given orientation such that the anchor plane 50 contains point 44 and is parallel to the bracket-slot-plane 48.

Define a current position $Z_n$; let n=0 and set $Z_n$ =$Z_0$.

Then,

1. Place the virtual bracket 42 on the exterior of the facial surface of the virtual tooth 40 such that the plane 47 passing through the center 46 of the slot 43 of the bracket 42 and orthogonal to the z axis is located at a distance 52 or $Z_n$ from the contact point 44 along the z axis and further that there are at least three points of contact between the bracket 42 base and the tooth 40 surface.

2. Calculate the resulting orientation and location of bracket-slot-plane 48.

3. Find the orthogonal distance 54 or $d_n$ from the bracket-slot-plane 48 to the anchor plane 50 which contains the occlusal tooth surface point or the contact point 44. (In the case where the tooth 40 is a molar or a premolar, restrict the search of the distances to the buccal part of the tooth.)

4. If the difference between the distance 54 or $d_n$ and the desired bracket height reference $bhr_z$, i.e. $\Delta_n$=$d_n$−$bhr_z$ lies in a given tolerance then stop the algorithm, else calculate the new z-height for the virtual bracket 42 position, $Z_{n+1}$=$Z_n$−$\Delta_n$, set n=n+1 and continue with step 1.

It will be appreciated that the calculations for placing the virtual bracket per the bracket height reference value specified by or selected by the user are required so as to make sure that the virtual bracket is positioned properly and securely when feasible, i.e., the base of the virtual bracket has at least three points of contact with the surface of the virtual tooth in view of the geometry and texture of the surface of the virtual tooth.

The above method of determining the bracket height reference for virtual bracket placement is given as an example. One skilled in art would understand that there exist numerous other alternative ways of determining the bracket height reference.

The bracket height reference may be specified by the user on a tooth-by-tooth basis, for groups of teeth, for all upper teeth, for all lower teeth, or for all upper and lower teeth.

The bracket height reference value may be varied, selectively when desired, to investigate the impact of different virtual bracket placements on the patient's treatment.

FIGS. 2(a)-2(d) illustrate- selection of the contact points and corresponding bracket height references for various categories of teeth. For the sake of simplicity in illustrations, the virtual anchor reference and the bracket height reference are shown as lines rather than planes.

For a canine tooth, FIG. 2(a) illustrates the canine tooth 60, the virtual bracket 61, the bracket-slot plane 62, the anchor plane 63, the contact point 64, and the bracket height reference 65. Here, the cusp tip is chosen as the contact point 64 for the anchor plane 63.

For a pre-molar tooth, FIG. 2(b) illustrates the pre-molar tooth 67, the virtual bracket 68, the bracket-slot plane 69, the anchor plane 70, the contact point 71, and the bracket height reference 73. Here, the labial cusp tip 71 is preferred as the contact point for the anchor plane 70, although the lingual cusp tip 72 offers an alternate contact point for the anchor plane.

For a molar tooth, FIG. 2(c) illustrates the molar tooth 75, the virtual bracket 76, the bracket-slot plane 77, the anchor plane 78, the contact point 79, and the bracket height reference 81. Here, the highest cusp tip 79 is chosen as the contact point for the anchor plane 78; although other alternatives such as, for example, any one of the cusp tips, or a point derived by averaging the heights of the molar cusp tips where such a point may not actually touch the tooth crown, are available for contact points for the anchor plane.

For an incisor tooth, FIG. 2(d) illustrates the incisor tooth 83, the virtual bracket 84, the bracket-slot plane 85, the anchor plane 86, the contact point 87, and the bracket height reference 88. For incisors, if the tooth crown edge is flat, then any point on the crown edge can be chosen as the contact point; otherwise the highest point on the tooth edge is chosen as the contact point for the anchor plane.

The contact point selection delineated herein through FIGS. 2(a)-2(d) is not meant to be exhaustive.

In another embodiment of the invention, the bracket placement reference is provided through a virtual bracket placement occlusal reference plane placed parallel to the virtual occlusal plane for the patient. Often, the occlusal plane reference provides a better vehicle than the bracket height reference for placing the virtual brackets on the virtual teeth of a patient organized in the target state. Once selected by the user, the occlusal plane reference is superimposed on the virtual teeth by the treatment planning unified workstation 28; and a capability is provided for the user to move it to a desired position for placement of the virtual appliances or brackets on the virtual teeth. The height and gradient of the virtual bracket placement occlusal reference plane can be changed by the user to investigate the impact of different virtual bracket placements with this reference on the patient's treatment, since the bracket placement done in this manner impacts torque applied to the teeth and provides the capability of moving teeth transversely. One virtual bracket placement occlusal reference plane is provided for the upper jaw, and the other for the lower jaw. In yet another embodiment, the virtual bracket placement occlusal reference plane can be viewed and manipulated in segments for groups of virtual teeth.

Figure 3:
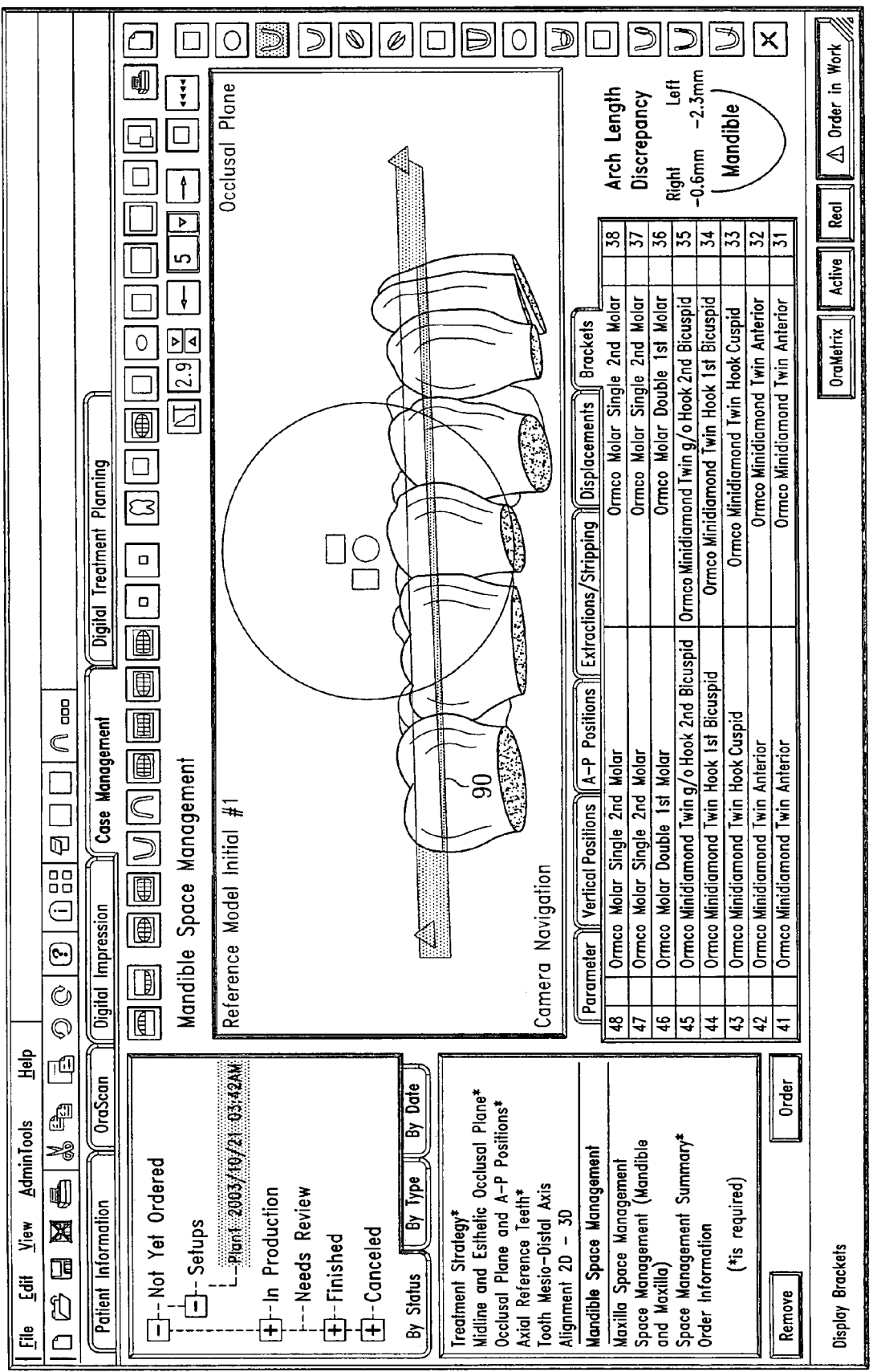
FIG. 3 illustrates virtual occlusal plane reference for placement of virtual appliances on virtual teeth according to one embodiment of the present invention.

FIG. 3 illustrates virtual bracket placement occlusal plane reference 90 for placement of virtual appliances on virtual teeth.

In yet another embodiment of the invention, the bracket placement reference is provided through a virtual bracket placement arbitrary reference plane which need not be flat. If the desired treatment results could not be achieved through the use of the bracket height reference or the occlusal plane reference, an orthodontist may resort to examining the effectiveness of the arbitrary plane as a reference for positioning the virtual brackets on the virtual teeth of a patient. Like the occlusal plane reference, once selected by the user, the arbitrary plane reference is superimposed on the virtual teeth by the treatment planning unified workstation; and a capability is provided for the user to move it to a desired position for placement of the virtual appliances or brackets on the virtual teeth. The height and shape of the virtual bracket placement arbitrary reference plane can be changed by the user to investigate the impact of different virtual bracket placements with this reference on the patient's treatment. One virtual bracket placement arbitrary reference plane is provided for the upper jaw, and the other for the lower jaw. In yet another embodiment, the virtual bracket placement arbitrary reference plane can be viewed and manipulated in segments for groups of virtual teeth.

Figure 4:
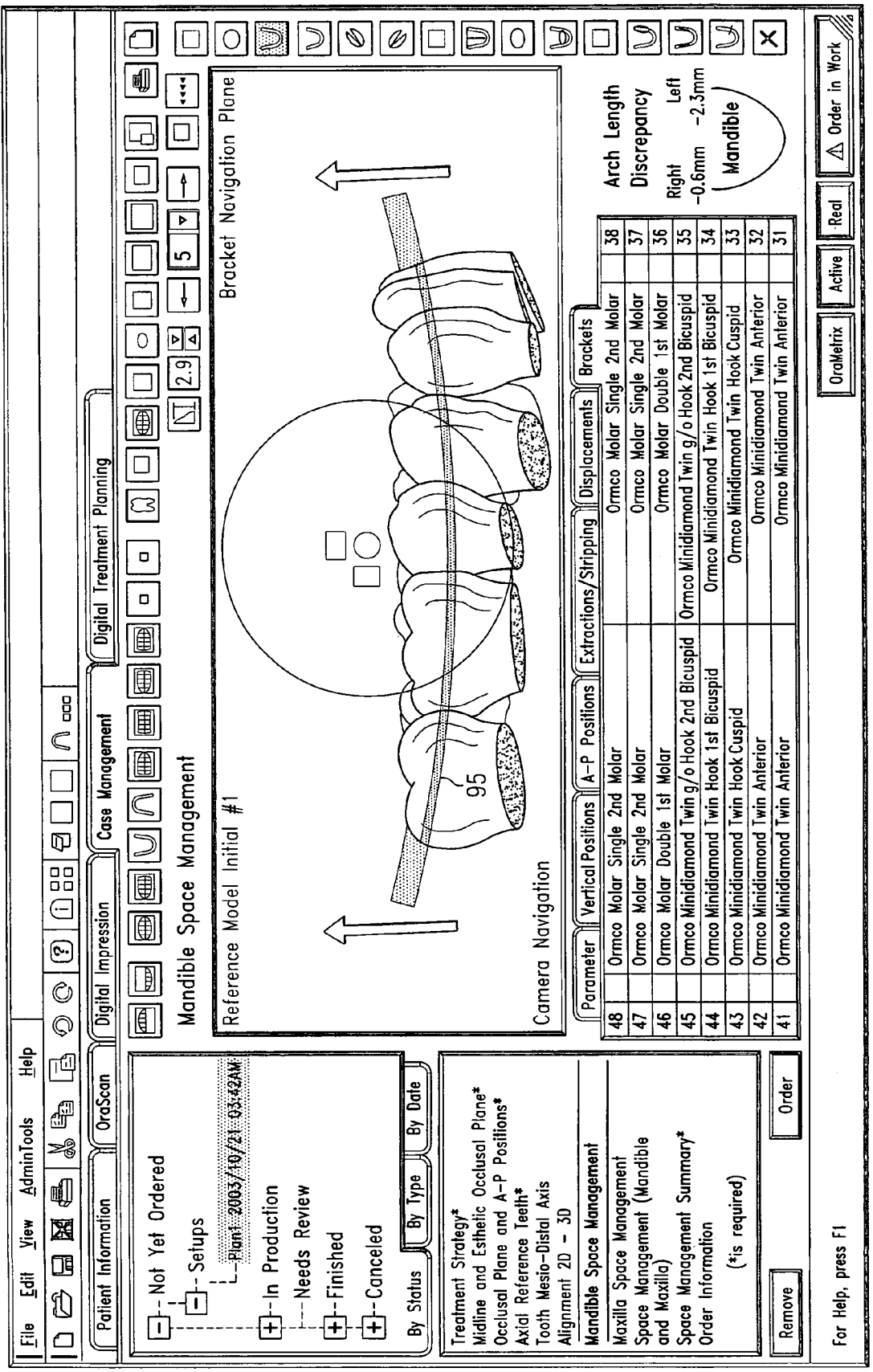
FIG. 4 illustrates virtual arbitrary plane reference for placement of virtual appliances on virtual teeth according to another embodiment of the present invention.

FIG. 4 illustrates a virtual bracket placement arbitrary plane reference 95 for placement of virtual appliances on virtual teeth.

The practitioner or the user can use any of the references described above, either singly or in combination, in accordance with his or her preference or medical condition of the patient, to place the virtual appliances on the virtual teeth as a starting set-up to work with. For example, the user may start out with the bracket height reference for the virtual bracket placement, and then verify results using the virtual occlusal plane bracket placement reference.

Figure 5:
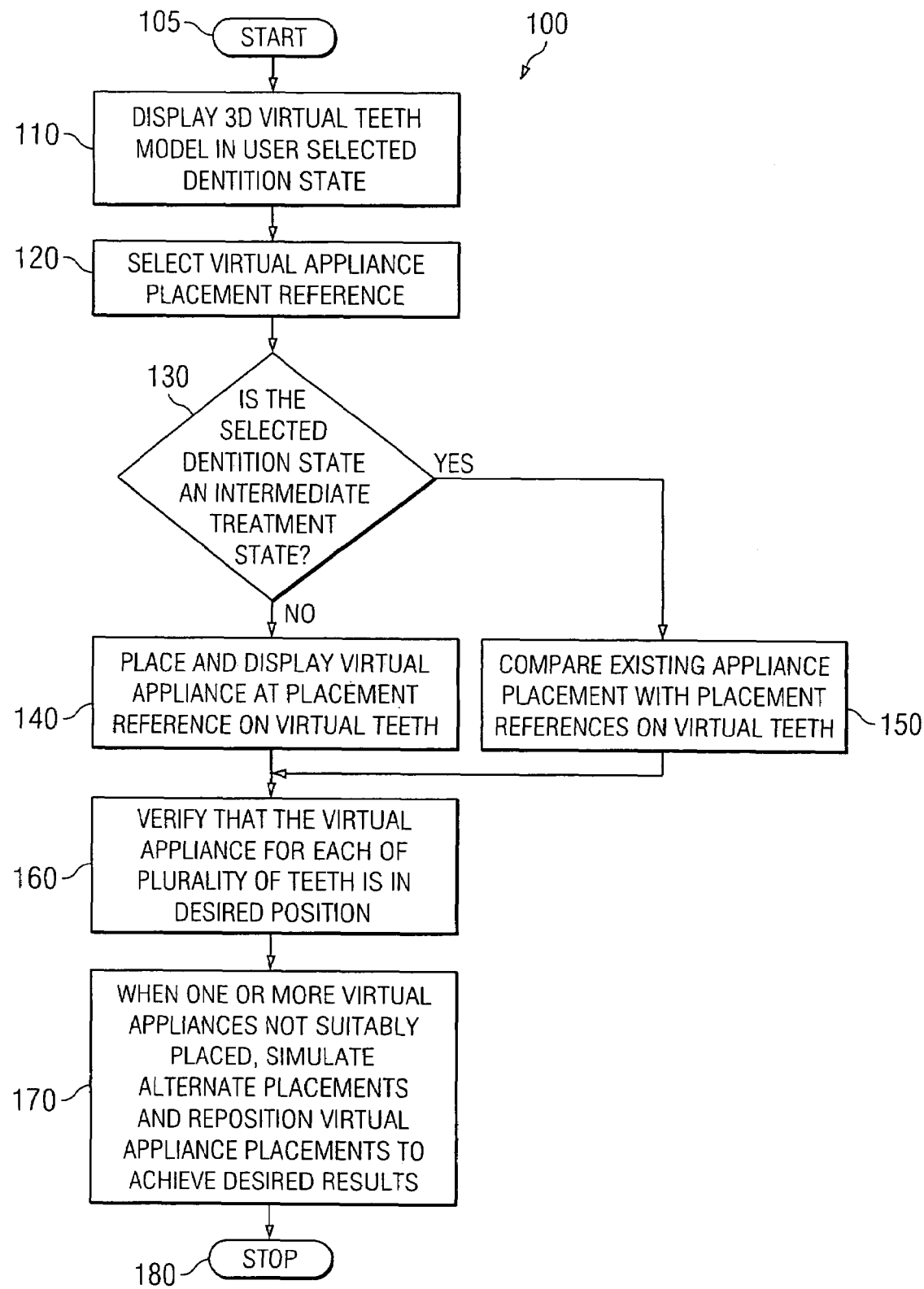
FIG. 5 is a flow chart illustrating the method of facilitating placement of virtual appliances at desired positions on virtual teeth of an orthodontic patient according to the present invention using a unified workstation having a processing unit, memory having a three-dimensional virtual model of teeth of the patient, and an user interface including a display and software executable by said processing unit.

The present invention is best understood by the flow chart 100 illustrated by FIG. 5. The method of facilitating placement of virtual appliances at desired positions on virtual teeth of an orthodontic patient using a previously described unified workstation 28 having a processing unit, memory having a three-dimensional virtual model of teeth of the patient, and an user interface including a display and software executable by said processing unit, begins at 105 start step.

Figure 6:
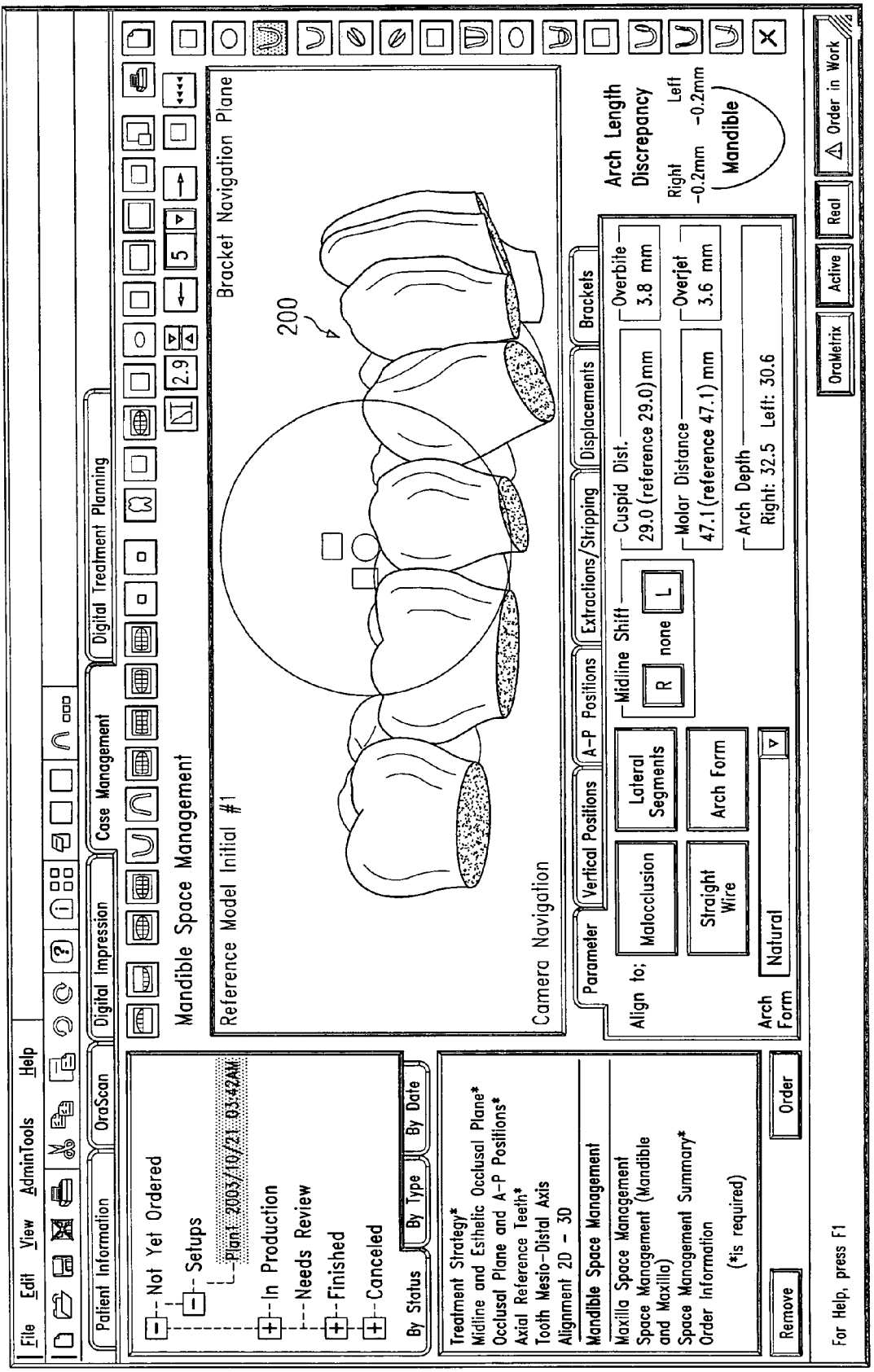
FIG. 6 is a screen shot depicting the patient's virtual teeth in the malocclusion state.
Figure 7:
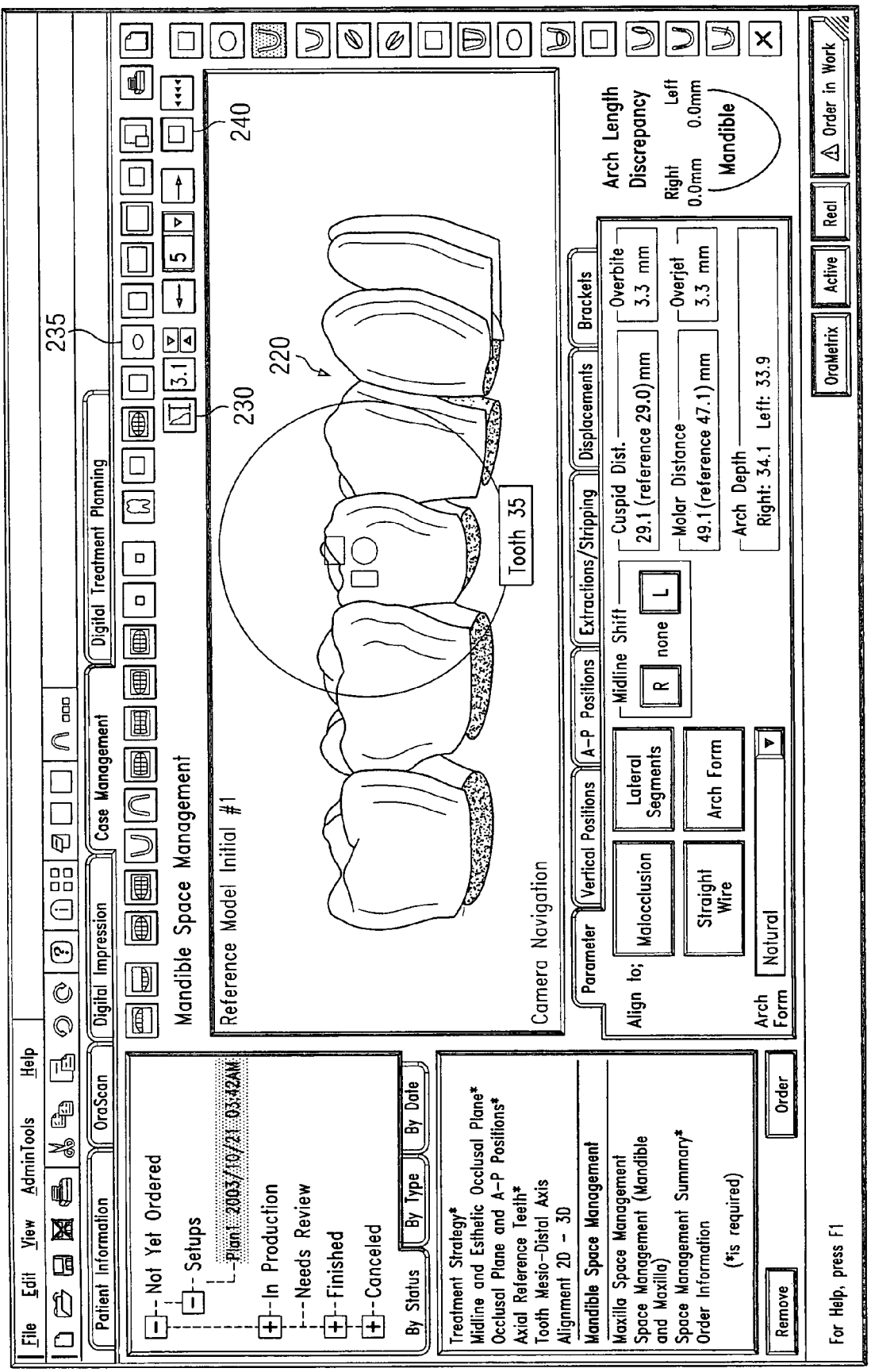
FIG. 7 is a screen shot depicting the patient's virtual teeth in the target state.
Figure 8A:
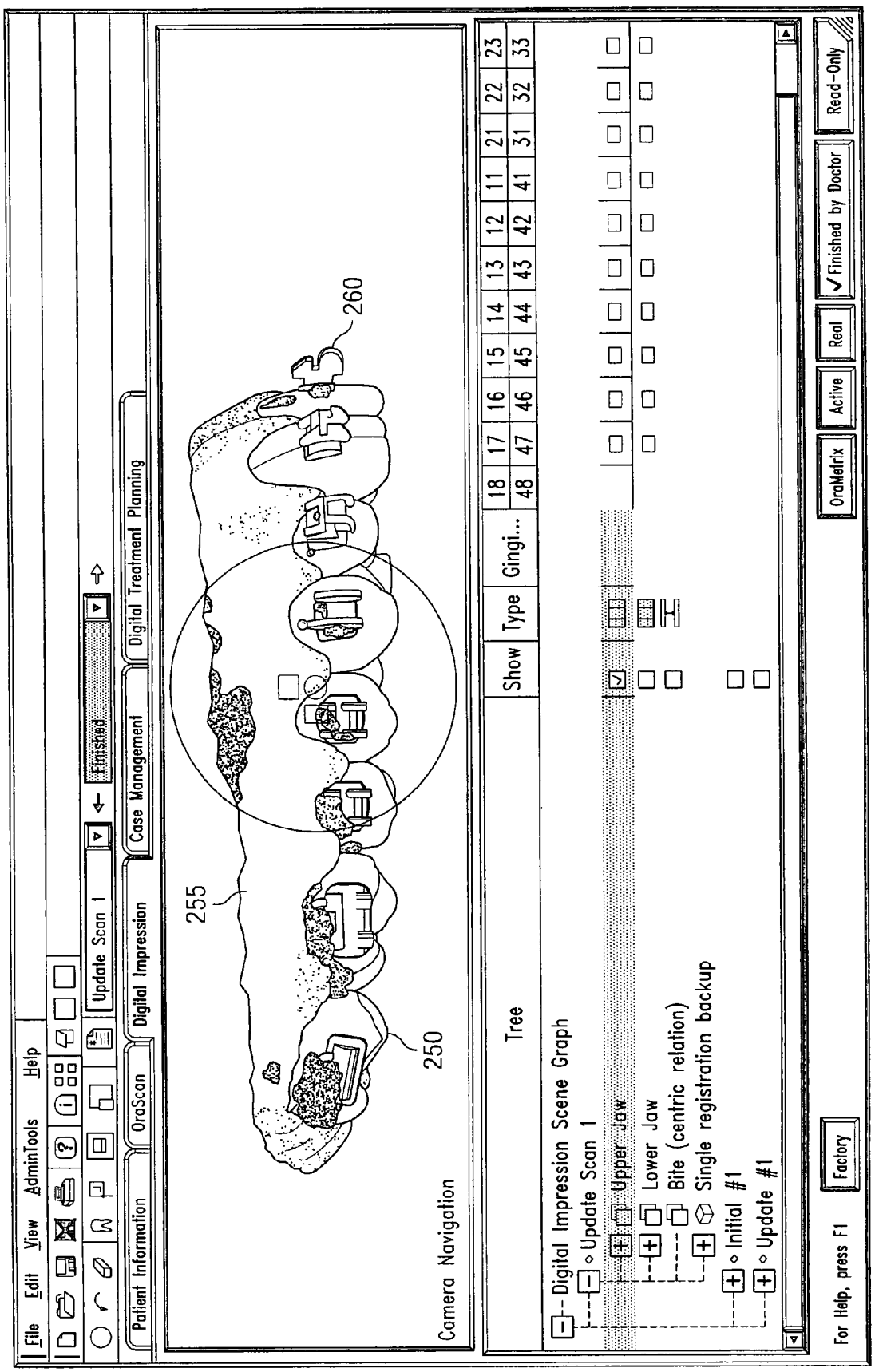
FIG. 8A depicts a screen display of the patient's dentition at the intermediate state obtained by in-vivo scan of the patient's teeth and gingiva along with the appliances or brackets placed on the teeth.
Figure 8B:
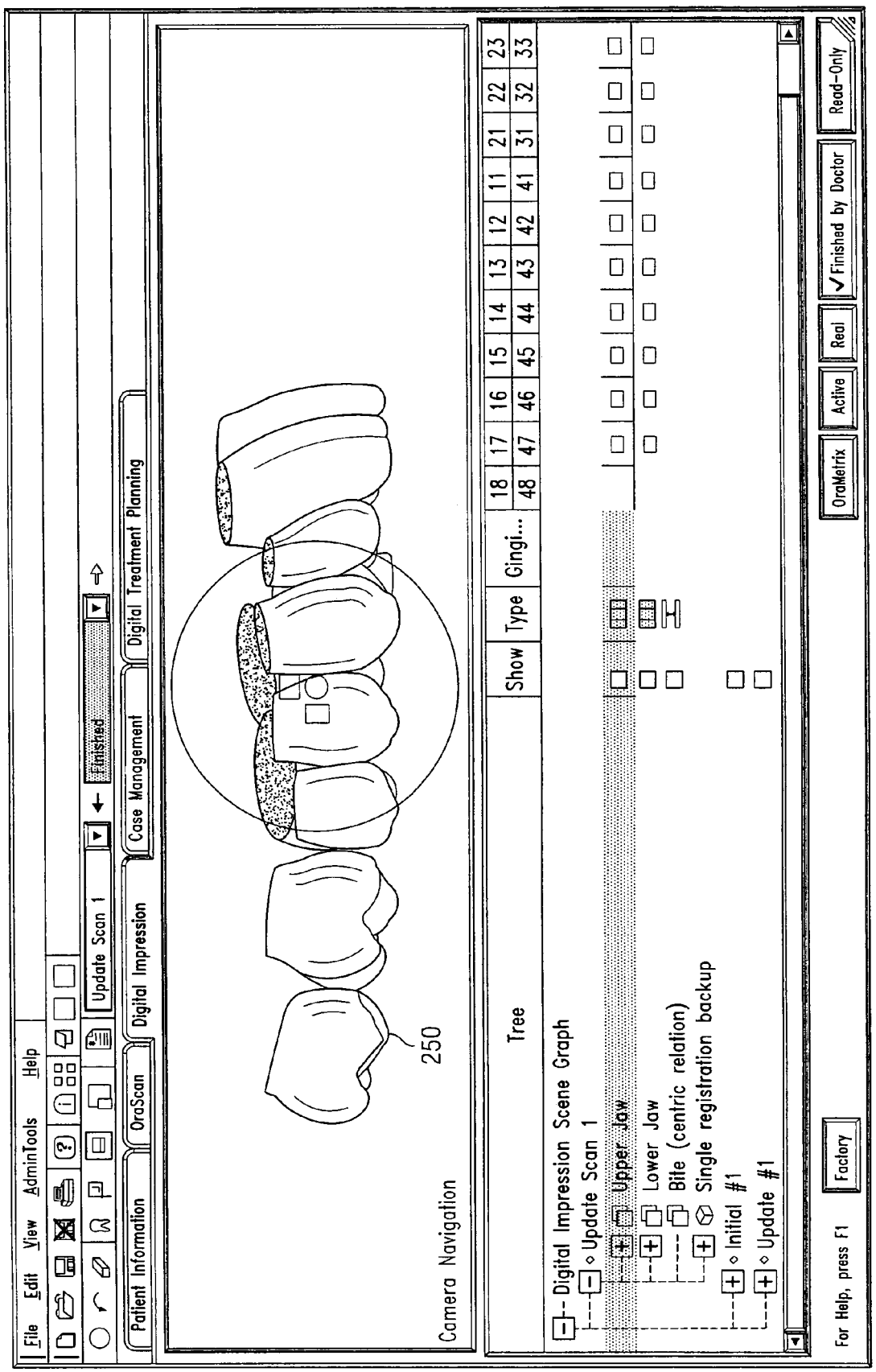
FIG. 8B depicts a screen display of a virtual three-dimensional model of the patient's teeth obtained by processing the scanned data from the model depicted in FIG. 8A.
Figure 8C:
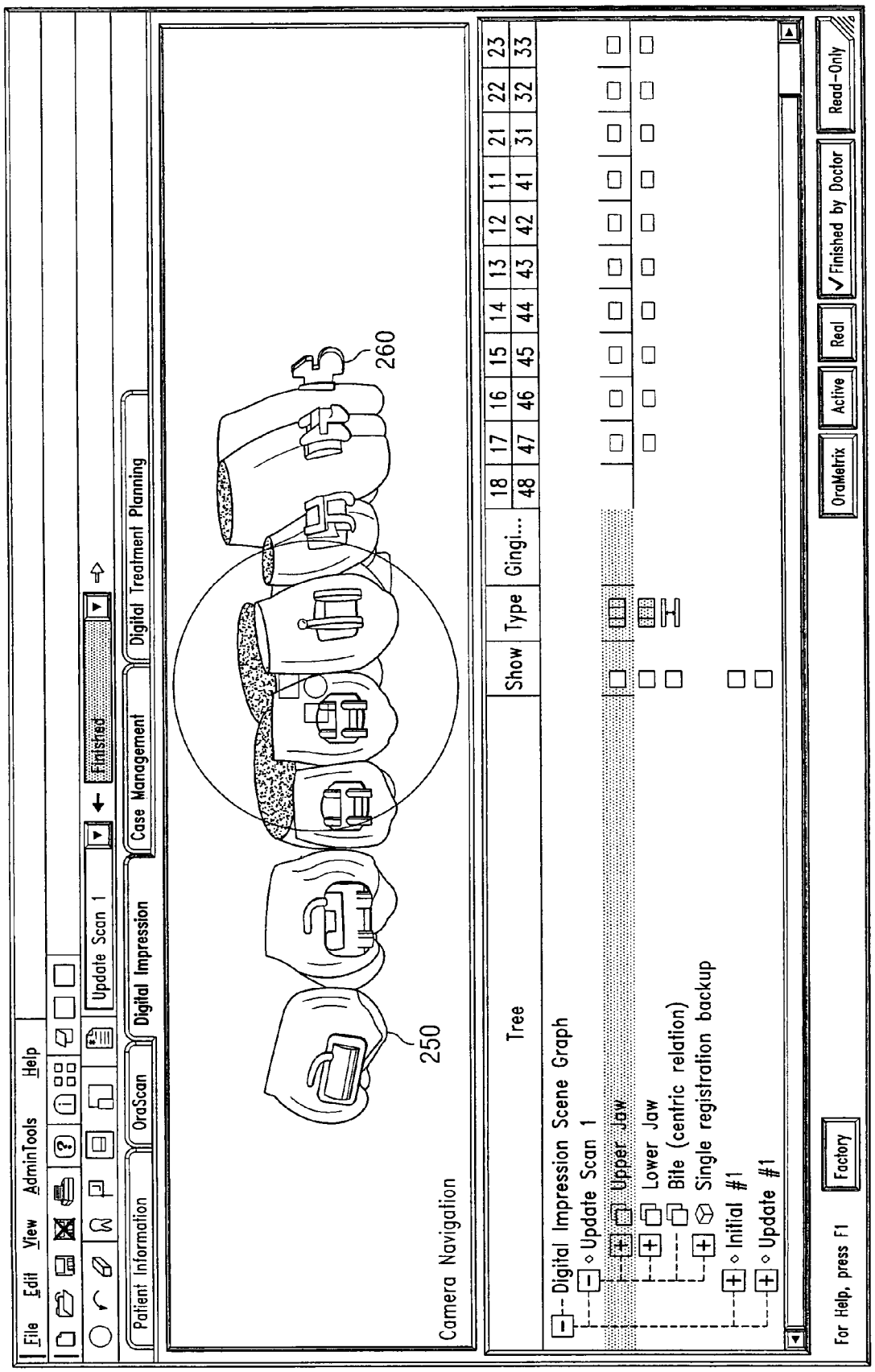
FIG. 8C depicts a screen display of a virtual three-dimensional model of the patient's teeth and brackets obtained by processing the scanned data from the model depicted in FIG. 8A.

At step 110 a three-dimensional virtual model of the teeth of a patient in a particular dentition state 18 is selected by the user or the practitioner and displayed on the screen display 30 of the unified workstation 28. Typically, the patient's malocclusion state 200 as depicted in FIG. 6 is selected at this step as the patient's dentition state. Alternately, the user selects at this step the virtual target dentition state 220 for the patient to be realized through the treatment as depicted in FIG. 7 as the dentition state to start the process. If a patient is already undergoing treatment, the user has the option at this step to select the intermediate treatment monitored state for the patient's dentition as the dentition state to start the process. If the treatment progress is unsatisfactory, the methodology described herein for the present invention can be utilized to investigate the desirability of repositioning the brackets on the patient's teeth at any intermediate stage during the treatment. First the patient's dentition at the intermediate state is obtained as depicted in FIG. 8A, for example, by in-vivo scan of the patient's teeth 250 and gingiva 255 along with the appliances or brackets 260 placed on the teeth 250. The unified workstation processes the scanned data to produce a virtual three-dimensional model of the patient's teeth 250 as illustrated in FIG. 8B; and teeth 250 along with the brackets 260 as illustrated in FIG. 8C. Each tooth and each bracket in the virtual three-dimensional model is defined as an object and can be manipulated independently.

Next, at step 120 the user selects a particular virtual appliance placement reference for placing the virtual appliances on the virtual teeth of the patient. Again referring to FIG. 7, it illustrates various options through selection icons. For example, icon 230 corresponds to the bracket height reference, and icon 235 to the occlusal plane reference, and icon 240 to the arbitrary bracket placement plane reference. When the bracket height reference is selected, the bracket height is also specified. The bracket height may be specified on a tooth-by-tooth basis, for groups of teeth, for all upper teeth, for all lower teeth, or for all upper and lower teeth. When the occlusal plane reference is selected, one virtual occlusal reference plane is provided for the upper jaw, and the other for the lower jaw. The virtual occlusal reference plane can be viewed and manipulated in segments for groups of virtual teeth. When the arbitrary plane reference is selected, one virtual arbitrary reference plane is provided for the upper jaw, and the other for the lower jaw. The virtual arbitrary reference plane can be viewed and manipulated in segments for groups of virtual teeth.

Next, at step 130 a determination is made whether the dentition state selected by the user at step 110 is an intermediate treatment state for the patient. If the dentition state selected by the user at step 110 is not an intermediate treatment state for the patient then the process moves to step 140; otherwise to step 150.

Figure 9:
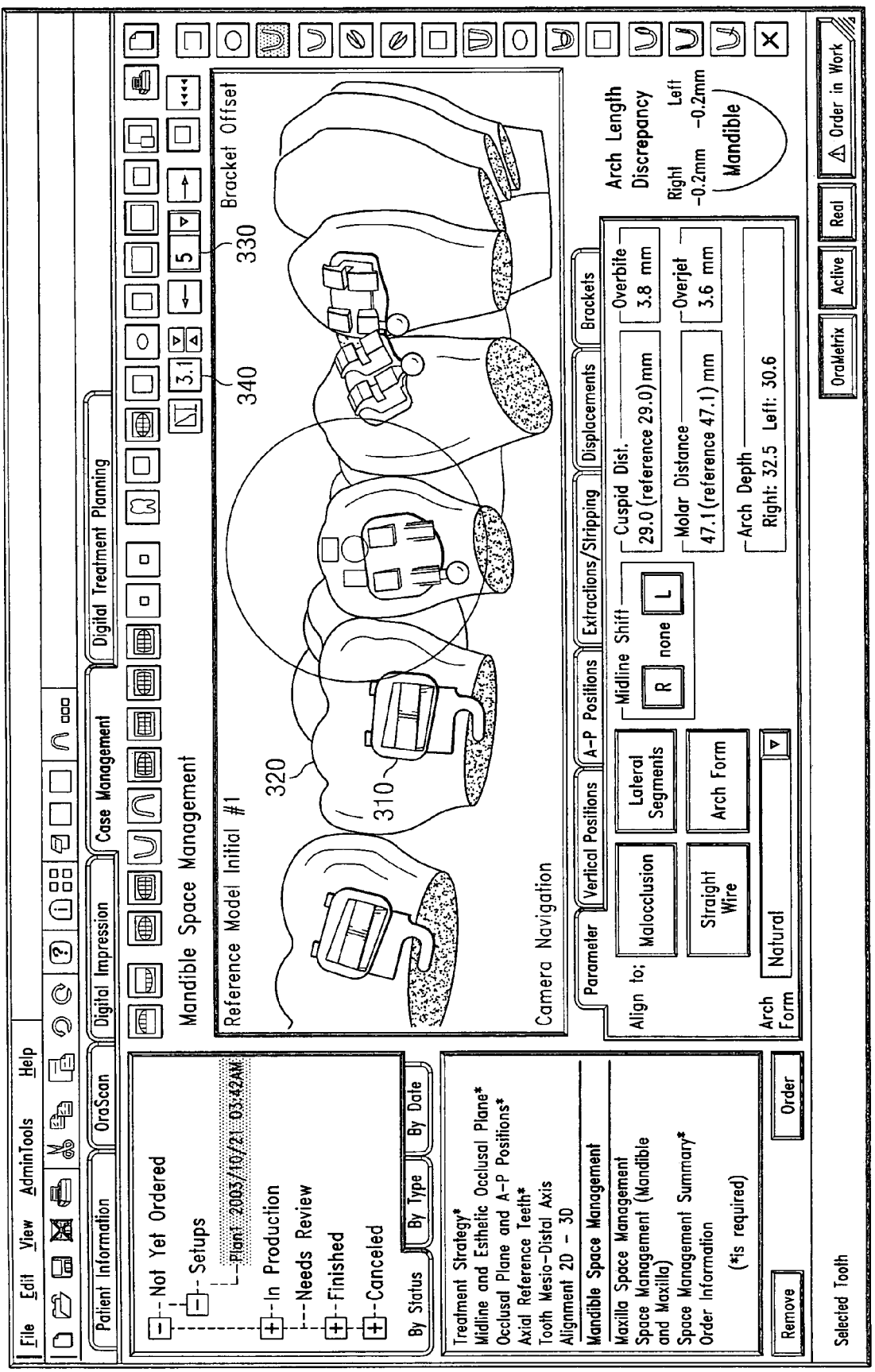
FIG. 9 depicts the placement of virtual appliances at the bracket height reference on plurality of the virtual teeth in the malocclusion state of a patient according to the present invention.

At step 140 virtual appliances are automatically placed on plurality of the virtual teeth in the dentition state selected by the user at step 110 at the virtual appliance placement reference selected by the user at step 120, and the combination of the virtual teeth with the virtual appliances placed upon them is displayed on the screen display 30 of the unified workstation 28. In the case of virtual brackets, they are placed on the virtual teeth as specified by the selected appliance placement reference such that the particular reference preferably intersects the bottom of the bracket slot in the middle and is parallel to the two flanks of the bracket slot. For example, the placement of virtual brackets 310 at the bracket height reference on plurality of the virtual teeth 320 in the malocclusion state of a patient is depicted in FIG. 9. FIG. 9 further illustrates tooth number at 330 and the corresponding bracket height at 340. Although not illustrated, the bracket height reference can be similarly utilized with the target dentition state; and the occlusal plane reference or the arbitrary plane reference can be similarly utilized with the malocclusion state and the target state of the patient's dentition. Typically, the virtual appliance is a bracket; although other virtual appliances, such as O-rings, are possible. The bracket may be per the prescription from the orthodontist or the practitioner, or it may be selected by the user from a library of brackets stored in the memory of the unified workstation 28 or in any other electronic storage device accessible by the unified workstation 28. All virtual brackets placed on the virtual teeth of a patient might be of the same type, or there might be a mixture of types. The process moves next to step 160.

At step 150, the patient's dentition in the intermediate treatment state is shown with the current virtual appliances attached and a comparison is made by the user between the existing appliance placement and the placement suggested by the virtual appliance reference. Although not illustrated, the intermediate treatment state for the patient can be made to work with bracket height reference as well as other virtual appliance placement references such as virtual occlusal plane reference or virtual arbitrary plane reference. The process moves next to step 160.

Thus at step 140 or step 150, the invention provides automatic placement of virtual brackets on plurality of virtual teeth in accordance with the pre-defined reference chosen by the practitioner or the user which takes into account recognized virtual teeth features.

Figure 10:
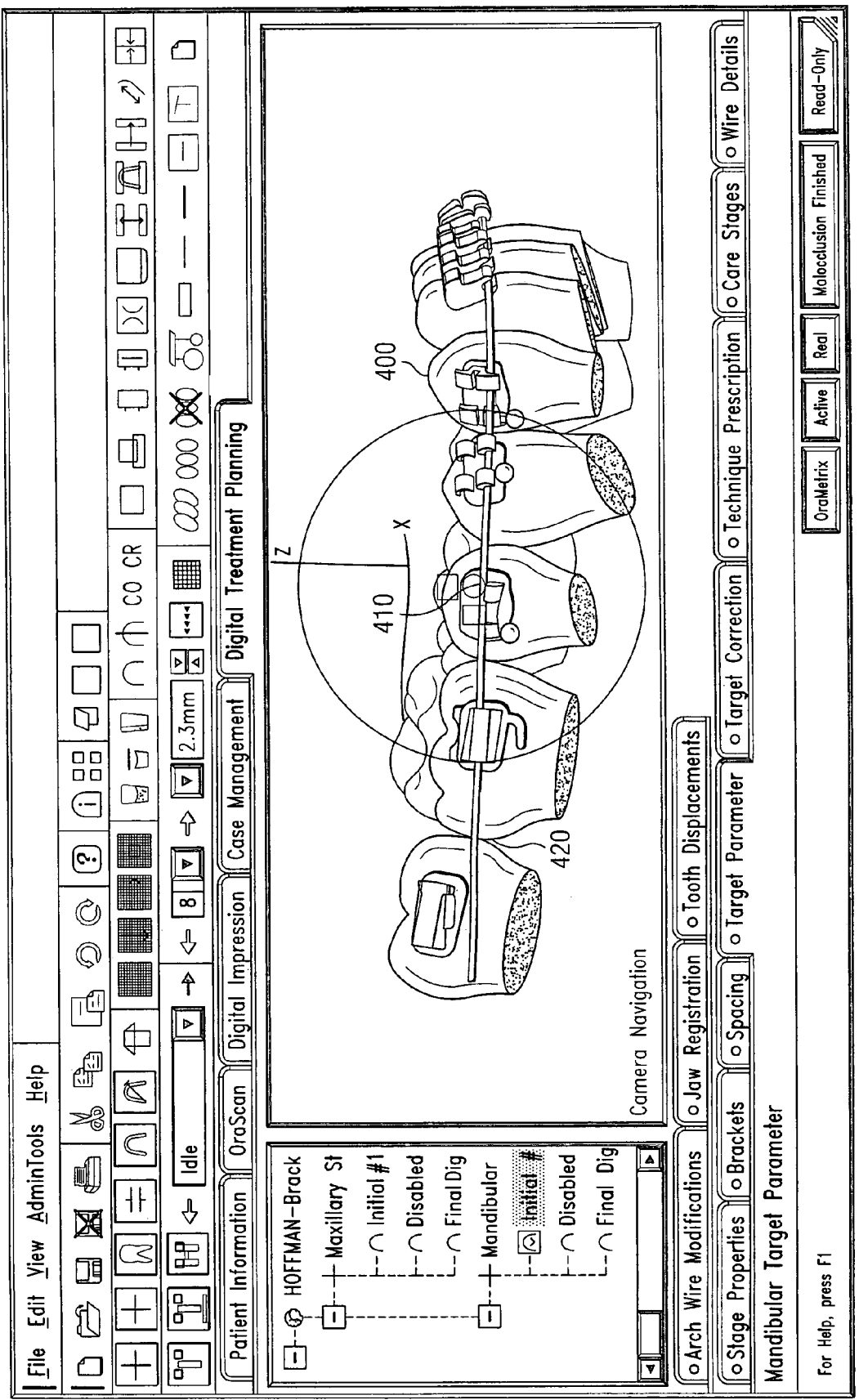
FIG. 10 illustrates virtual teeth of a patient in malocclusion state with virtual brackets placed upon the virtual teeth in the desired position and a straight archwire designed to bring the teeth into target state when fully inserted into all the bracket slots according to the present invention.
Figure 11:
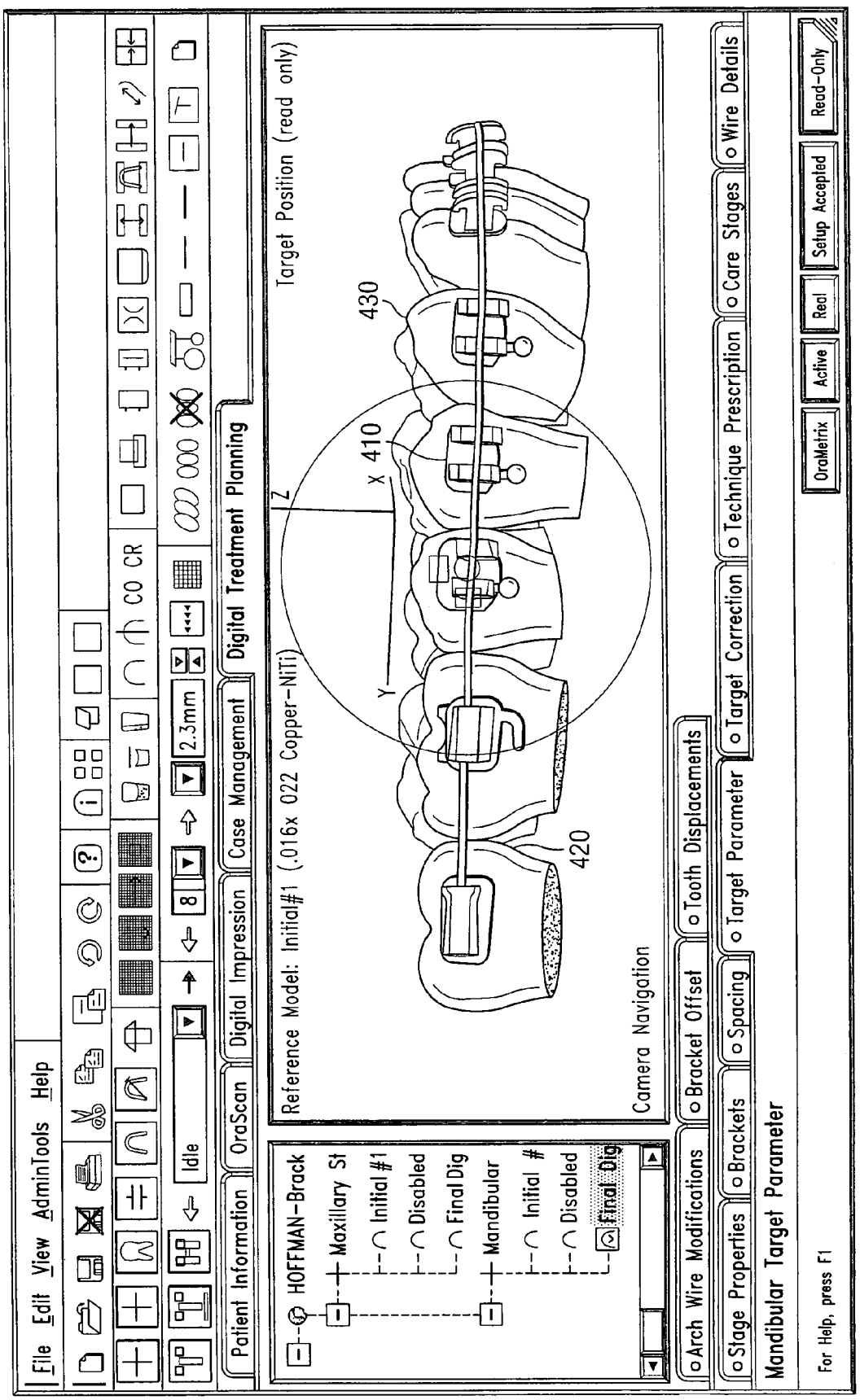
FIG. 11 illustrates the transformation of the malocclusion state of FIG. 10 into the target state.
Figure 12:
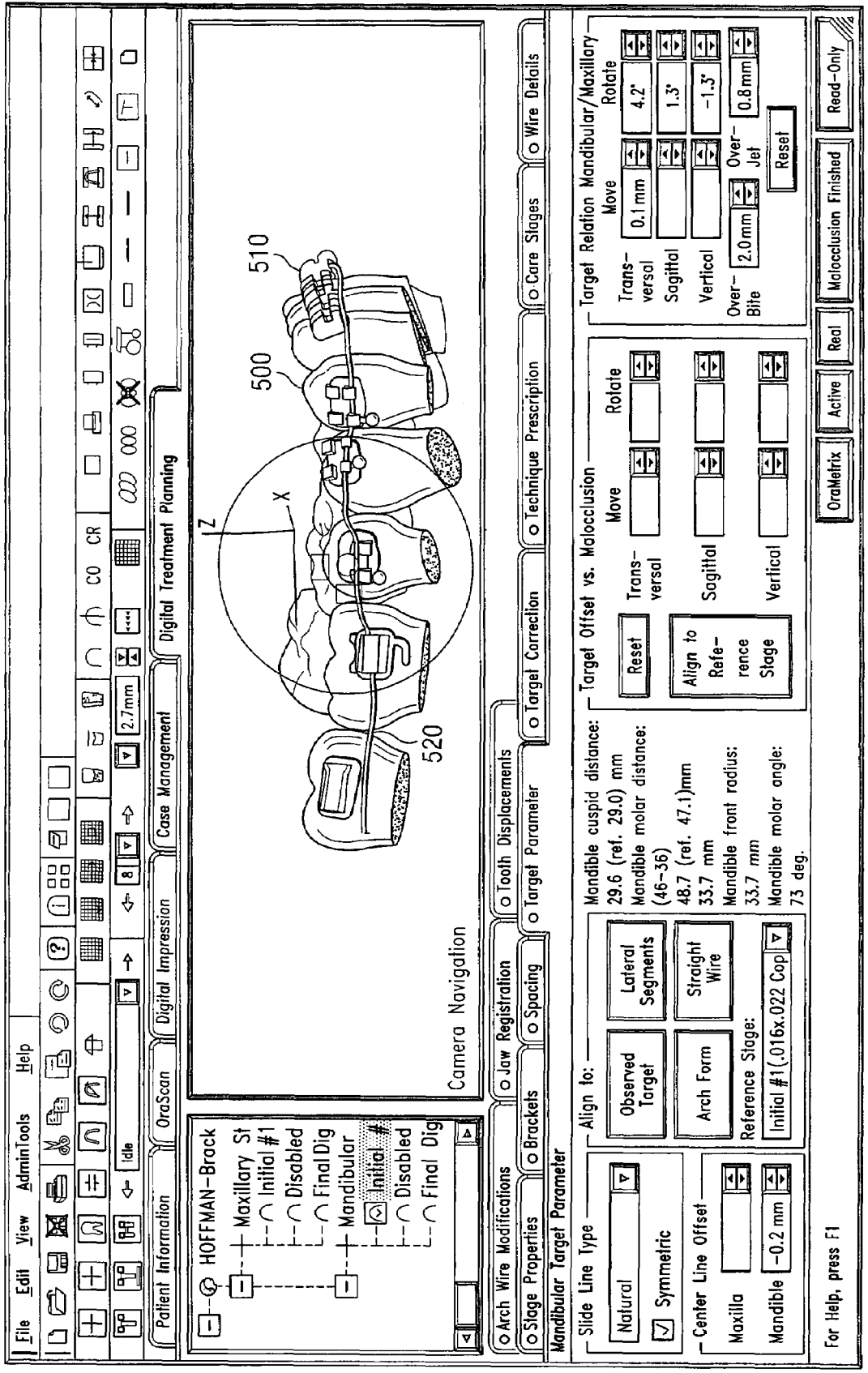
FIG. 12 illustrates virtual teeth of a patient in malocclusion state with virtual brackets placed upon the virtual teeth in the desired position and a hybrid archwire designed to bring the teeth into target state when fully inserted into all the bracket slots according to the present invention.
Figure 13:
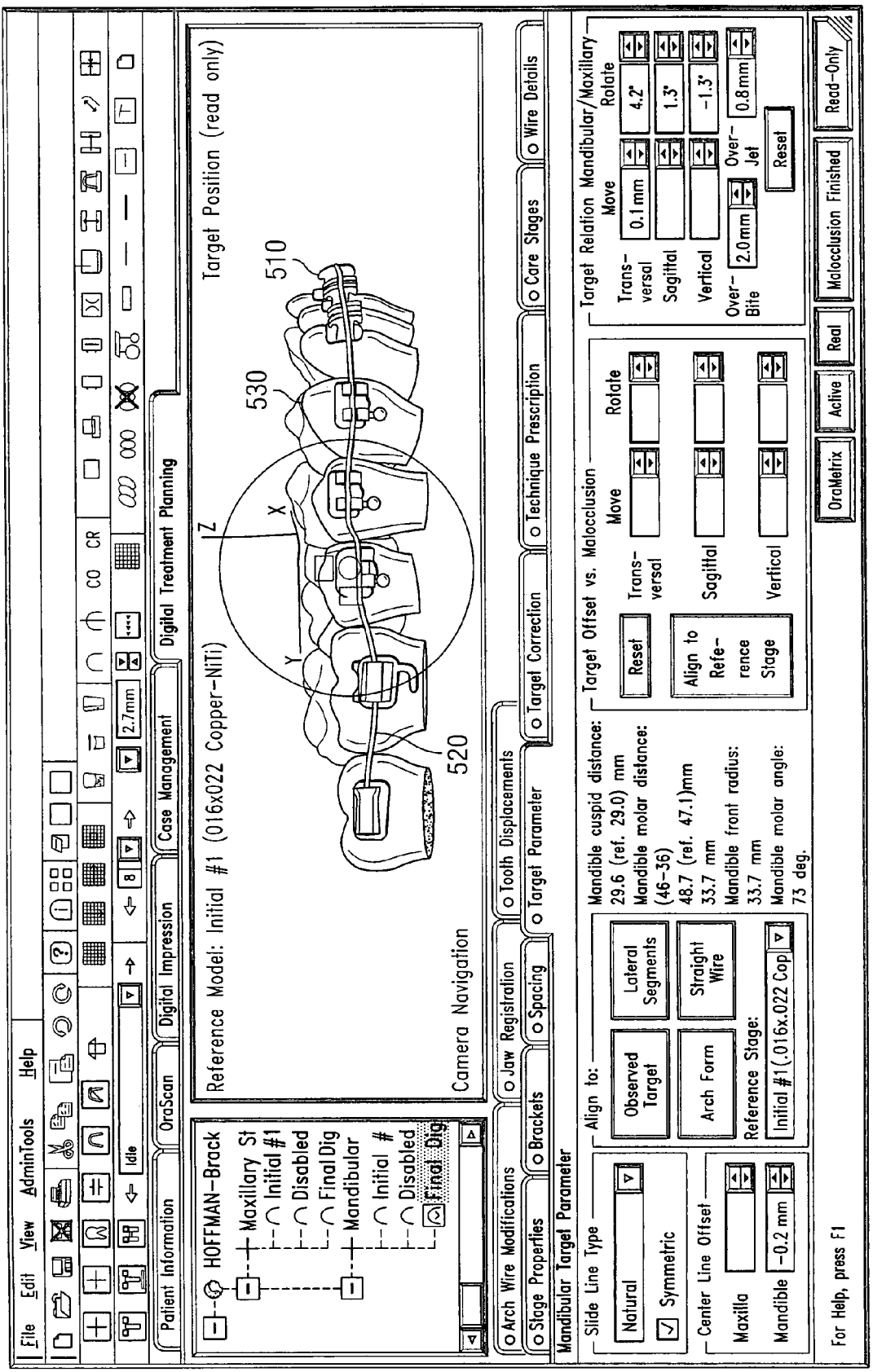
FIG. 13 illustrates the transformation of the malocclusion state of FIG. 12 into the target state.

At step 160, the virtual appliance placement for each of said plurality of virtual teeth is verified to ascertain that it is in the desired position. The verification process comprises examining the virtual appliance placement locally for each virtual tooth, for selected groups of virtual teeth, and globally for all virtual teeth. The verification process is very comprehensive and includes numerous steps such as, but not limited to, detecting penetration of the virtual teeth by in appropriate placement of the virtual brackets and collision between brackets; ascertaining that the bracket is placed on the center of the labial surface of the tooth; in viewing the bracket placement using the clipping plane tool of the workstation 28 that enables looking at the cross-sections and in ascertaining that the bracket is properly adapted to the labial surface of the tooth; in viewing the bracket placement in relation to the occlusion plane and ascertaining that the brackets are placed properly; in checking the placement height, angulation, and torque of each bracket; in ascertaining that the resulting marginal ridges are lined-up; in ascertaining that the cusp tips are in the desired position; in verifying the design of the archwires for the upper and lower jaws in light of the bracket placements. The virtual bracket placement and the virtual archwire combination or set-up can be thoroughly verified and evaluated using software tools in the workstation 28. For example one set-up may be done with a straight archwire, and another with a customized archwire having a series of bends, and yet another with a hybrid archwire comprising selective use of straight archwire segments interspersed with customized bends. Rotation of the virtual archwire in the virtual bracket slots can be simulated as well. Various alternatives of the virtual bracket placement and the virtual archwire configuration are evaluated through simulation so that the final results are the desired results that avoid misplacement of the brackets. FIG. 10 illustrates virtual teeth of a patient in malocclusion state 400 with virtual brackets 410 placed upon the virtual teeth in the desired position and a straight archwire 420 designed to bring the teeth into target state when fully inserted into all the bracket slots. The transformation to the target state 430 is illustrated in FIG. 11 wherein the brackets 410 and the straight archwire 420 are the same as in FIG. 10; however, unlike FIG. 10, the arch wire in this case is inserted into slots of all the brackets. Similarly, FIG. 12 illustrates virtual teeth of a patient in malocclusion state 500 with virtual brackets 510 placed upon the virtual teeth in the desired position and a hybrid archwire 520 designed to bring the teeth into target state when fully inserted into all the bracket slots. The transformation to the target state 530 is illustrated in FIG. 13 wherein the brackets 510 and the hybrid archwire 520 are the same as in FIG. 12; however, unlike FIG. 12, the archwire in this case is inserted into slots of all the brackets. Although not illustrated by way of a figure, similar set-up arrangements using a virtual customized archwire in conjunction with suitable virtual brackets and their desired placement on a plurality of virtual teeth of a patient are possible with the present invention. The workstation 28 provides software tools to indicate conflicts, if any, between virtual brackets and virtual teeth on malocclusion and between virtual brackets and virtual teeth and virtual archwire on target setup.

Figure 14:
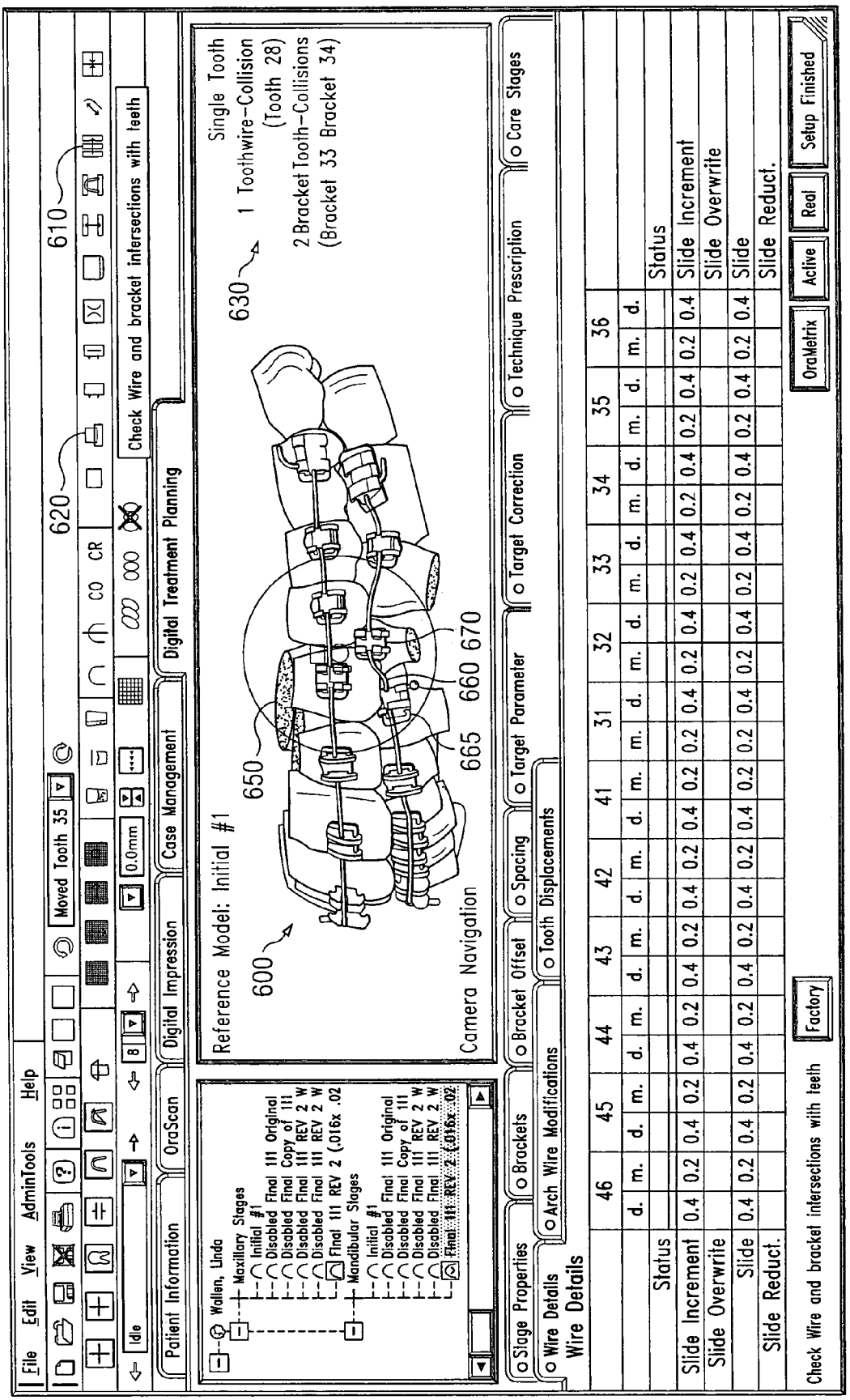
FIG. 14 illustrates (a) an user selectable button on the toolbar of the screen display on the workstation in order to perform penetration and collision checks in accordance with the present invention, (b) tooth-wire collision, (c) bracket-tooth collision, and (d) an example of a collision report on the screen display listing each collison in accordance with the present invention.

As illustrated in FIG. 14, the user selects button 620 on the toolbar 610 of the screen display 600 on the workstation 28 in order to perform penetration and collision checks. For example, the following checks of the current stage are performed.
  a) Each bracket is tested against the neighboring teeth for detecting potential collision.
  b) Each bracket is tested against the teeth of the opposite jaw for detecting potential collision.
  c) Each bracket is tested against the wire of the opposite jaw for detecting potential collision.
  d) Each tooth is tested against the wire of the opposite jaw for detecting potential collision and penetration.

Following the checks, for example, a collision report is displayed on the screen display listing each penetration as illustrated in FIG. 14 at 630. The penetrations are divided into 3 categories: (a) Tooth-Wire-Collisions, (b) Bracket-Wire-Collisions, and (c) Bracket-Tooth-Collision. For each category of collisions, teeth or brackets are listed and marked with a color-coding, not shown in FIG. 14, to point to the area of attention. This reporting scheme is simply an example, and one skilled in art would appreciate that other schemes are possible. FIG. 14 further illustrates a tooth-wire collision between tooth 23 shown at 650 and archwire 660; and bracket-tooth-collisions at bracket 33 shown at 665 and bracket 34 shown at 670.

Referring again to FIG. 5, next at step 170, when one or more virtual appliances are determined, through simulations, to be not suitably placed or not placed at the desired locations from the perspective of the ultimate treatment results, the workstation 28 enables the user to reposition the virtual appliances, and the alternate placements are evaluated using the simulation software in the unified workstation 28. Thus an interactive capability for the user is provided by the workstation 28. Using the simulation software routines in the workstation, solutions are found by digitally simulating alternate placements for the virtual appliances and adapting the archwire designs accordingly to rectify the problems discovered at step 160, and the placement of the virtual appliances are repositioned or modified in order to achieve the desired placements and the treatment results.

Figure 15:
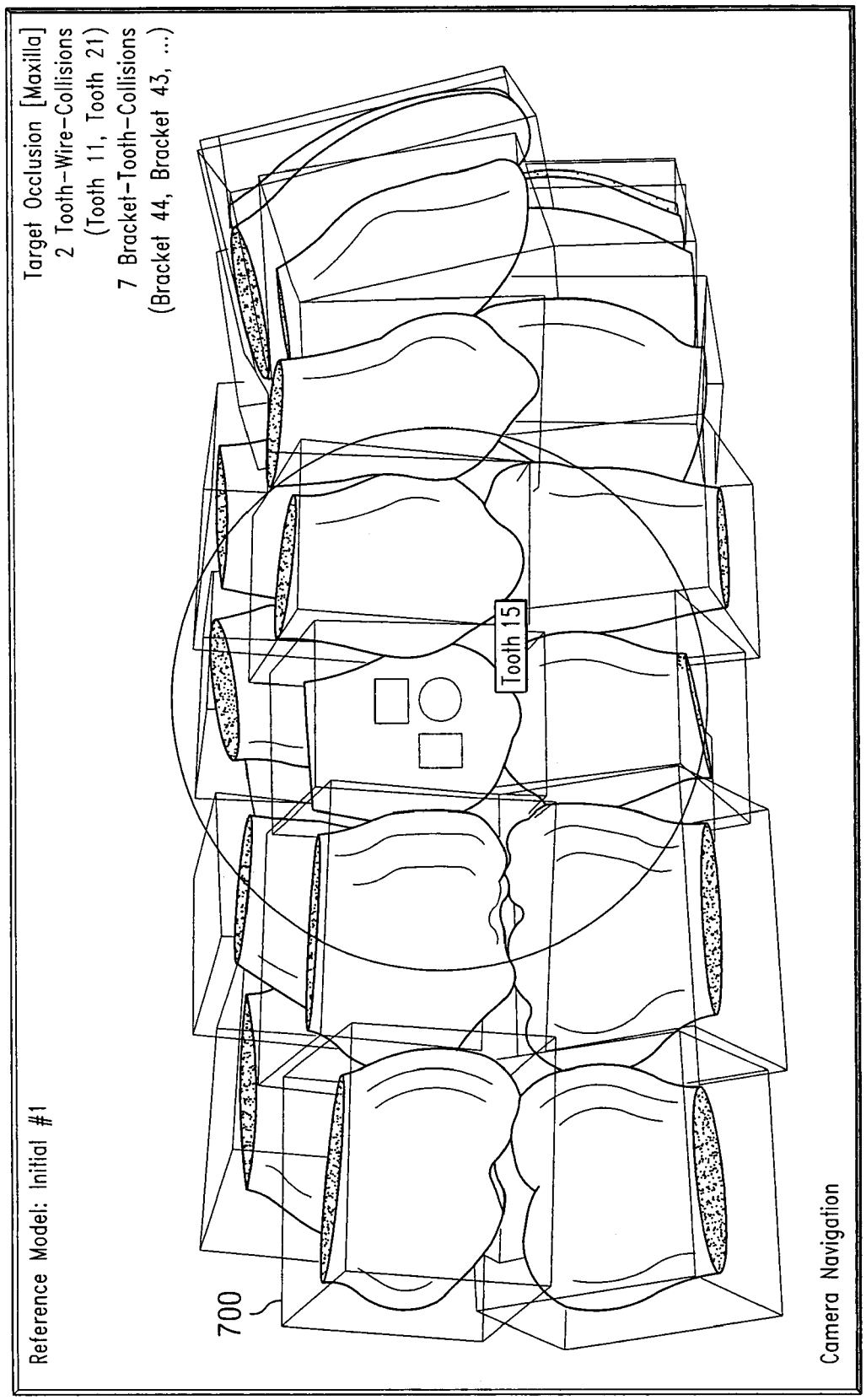
FIG. 15 illustrates viewing the virtual teeth enclosed by boxes in order to determine the desirability of the virtual teeth positioning, in accordance with the present invention.

There are numerous other software tools in the unified workstation 28 that enable the practitioner or the user in the verification and the simulation processes described above. These software tools provide the capability of moving individual virtual tooth, moving or repositioning individual virtual appliance, changing the type of the virtual appliance on a single tooth basis, modifying the archwire design, automatically measuring and marking the placement of the virtual appliances in relation to the surface of the virtual teeth in 2D and 3D; enabling the user in measuring and marking the placement of the virtual appliances using the graph paper display in 2D and 3D; measuring thickness of the gap between the bracket and the tooth surface for placing an adhesive pad; displaying the teeth in the virtual model in the form of a two-dimensional (2D) panorax with axial inclination for each tooth, enabling the practitioner or the user in modifying the placement of appliances, simulating its overall treatment effectiveness on the patient, and when a desired placement is achieved wrapping the virtual 2D model in three-dimensional (3D) view; moving the virtual bracket to realize proper adaptation of the virtual bracket to the surface of the virtual tooth; modifying the virtual bracket placement by moving the bracket to realize proper placement to remove any penetration of the bracket from the surface of the tooth; modifying the virtual bracket placement by moving the brackets to realize the desired relationship between the brackets and the occlusal plane wherein the occlusal plane could be the upper occlusal plane, the lower occlusal plane, or any one or more arbitrary sections of the upper and/or lower occlusal plane selected by the user; changing the level of the occlusal plane and simulating its overall treatment effectiveness on the patient; changing the angle of the occlusal plane and simulating its overall treatment effectiveness on the patient; simulating changes in the placement height, angulation, and torque of the bracket and evaluating its overall treatment effectiveness on the patient; modifying the virtual bracket placement by moving one or more brackets so that the marginal ridges are aligned in a desired position; moving one or more virtual brackets or in order to realize the desired positions of the cusp tips; enabling the practitioner in placing the bracket such that the selected reference tooth is blocked from moving and simulating its overall treatment effectiveness on the patient; enabling the practitioner or the user in viewing only the selected objects such as the virtual teeth, the virtual appliances, or the virtual archwire or a combination of objects and hiding the remaining objects from the view, e.g., viewing the virtual brackets alone and hiding the virtual teeth from the view; simulating the effectiveness of the archwire configuration and making adjustments when necessary to realize the desired position of the patient's digital teeth; viewing the virtual teeth enclosed by boxes 700 as illustrated in FIG. 15 to determine the desirability of the virtual teeth positioning.

Once the virtual brackets are placed, the invention provides software tools for easy adjustment of the bracket placement. The workstation 28 provides the capability for simulating the effectiveness of the straight wire treatment coupled with the virtual bracket placements in producing the desired treatment results. The workstation 28 provides software tools to create treatment setup alternatives based upon the initial and the adjusted virtual bracket placements. The simulation capability can lead to improved results from straight wire treatment. The bracket placements can be optimized according to a target setup. The bracket placements can be optimized according to interplay between straight archwire and customized archwire. The desired bracket placement can simplify shape of the custom archwire by reducing the severity of the bends so that insertion of the archwire into the bracket slots is easier.

Many of the treatment planning, simulation, and verification tools pertinent to the present invention are described in the patent application of Rohit Sachdeva et al. filed on Jul. 14, 2003, entitled METHOD AND SYSTEM FOR COMPREHENSIVE EVALUATION OF ORTHODONTIC TREATMENT USING UNIFIED WORKSTATION Ser. No. 10/620,231, the contents of which are incorporated by reference herein, and therefore a more detailed discussion is omitted.

Figure 16:
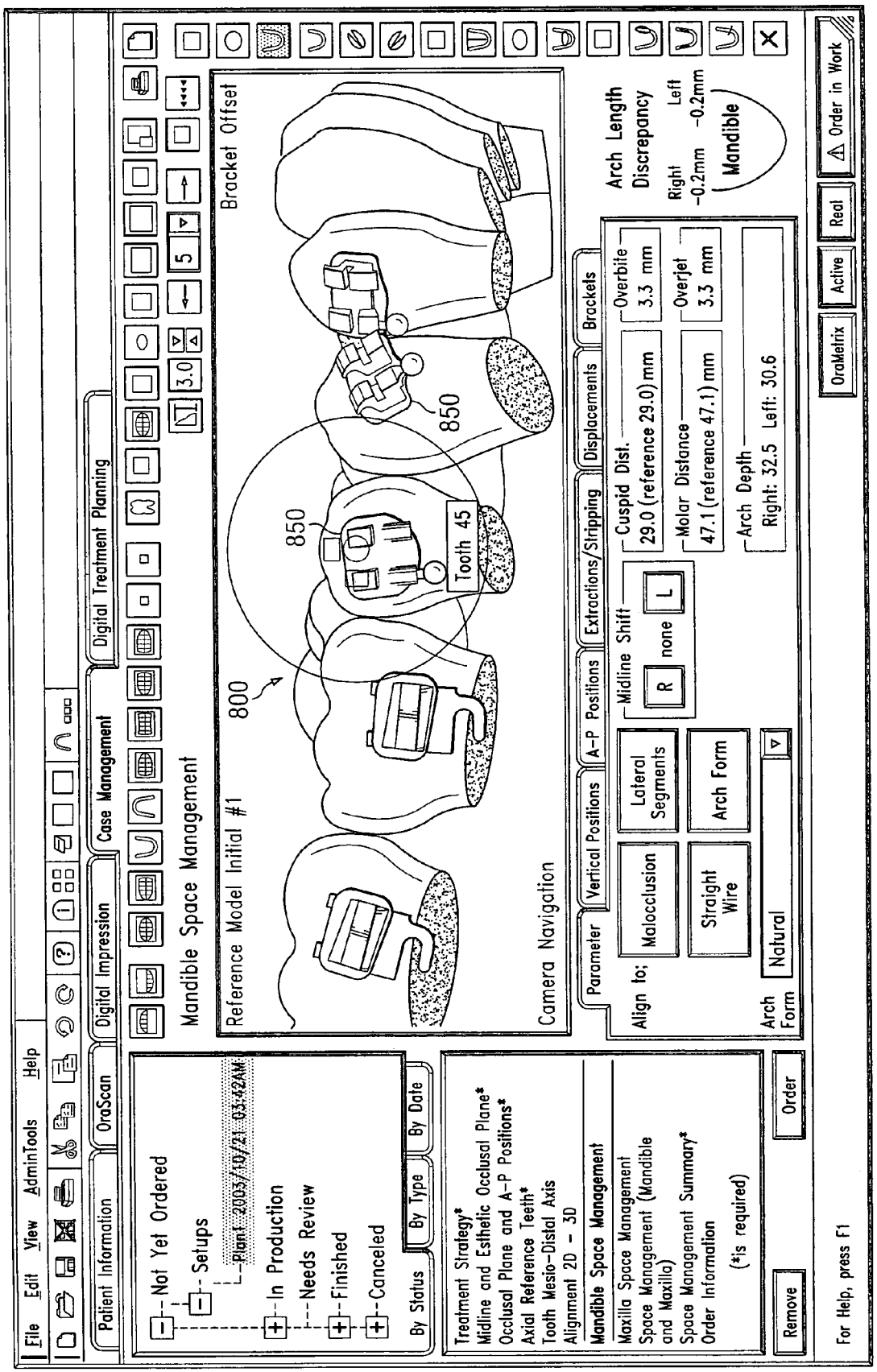
FIG. 16 illustrates the desired placement of the virtual appliances on the virtual teeth with bracket height as a virtual placement reference for a patient in malocclusion dentition state.
Figure 17:
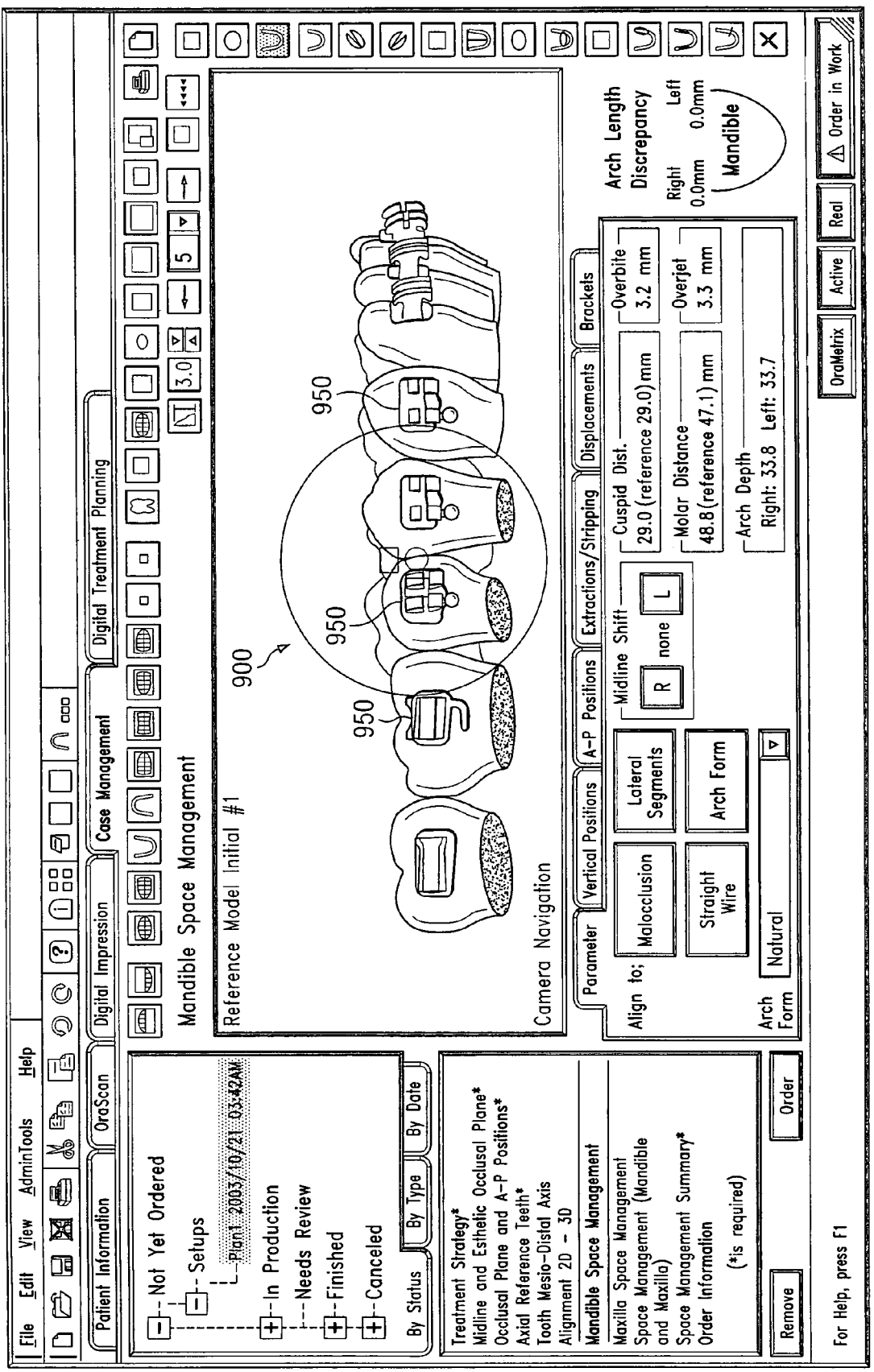
FIG. 17 illustrates the desired placement of the virtual appliances on the virtual teeth with bracket height as a virtual placement reference for a patient in the treatment target dentition state.
Figure 18:
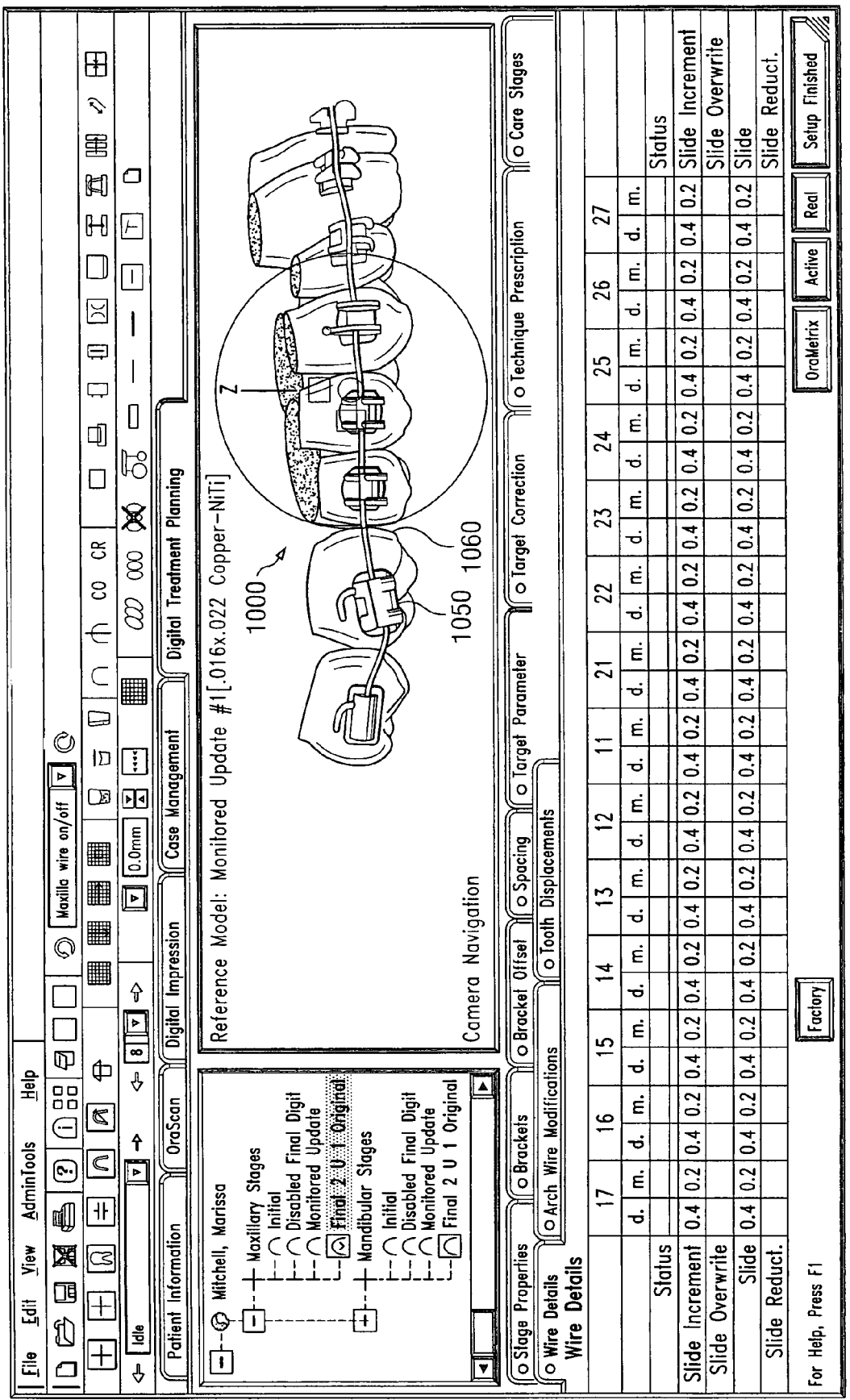
FIG. 18 illustrates the desired placement of the virtual appliances on the virtual teeth with bracket height as a virtual placement reference for a patient at an intermediate treatment dentition state according to the present invention.

Once the desired placements of the virtual appliances on the virtual teeth of the patient are realized the process stops at step 180. The desired placement of the virtual appliances on the virtual teeth is illustrated with bracket height as a virtual placement reference in FIG. 16 for a patient in malocclusion dentition state 800 with the virtual brackets 850, in FIG. 17 for a patient in the treatment target dentition state 900 with the virtual brackets 950, and in FIG. 18 for a patient at an intermediate treatment dentition state 1000 with the virtual brackets 1050 and the arch wire 1060; all according to the present invention. Although not illustrated, one skilled in the art would realize that the present invention equally applies to the other virtual references for the placement of the virtual appliances on the virtual teeth of a patient in various dentition states of a patients previously described.

The present invention provides a closed-loop capability for the virtual appliance placement on the virtual teeth of a patient and evaluation thereof through the use of the references discussed earlier, namely, the appliance height reference, the occlusal plane reference, and the arbitrary plane reference starting with initial malocclusion state of the patient or the target state of the patient and continued throughout the treatment through the intermediate monitored state of the patient.

An embodiment of the present invention comprises an apparatus for facilitating placement of virtual appliances at desired positions on virtual teeth of an orthodontic patient, comprising:

a workstation having a processing unit and a display;

a memory accessible by the workstation storing a virtual three-dimensional model of teeth and/or associated anatomical structures representing the dentition of a patient;

software executable by the processing unit to access the model and display the model on the display; and the software further including navigation tools enabling the user to interactively:

(a) display the three-dimensional virtual teeth model of a patient in the user selected dentition state of a patient;

(b) select a virtual appliance placement reference for placing virtual appliances on the virtual teeth;

(c) place and display the virtual appliance at the appliance placement reference on the plurality of the virtual teeth in the user selected dentition state;

(d) verify and evaluate that the virtual appliance placement for each of the plurality of virtual teeth is in desired position; and (e) when one or more of the virtual appliances are not suitably placed or not placed at the desired positions, digitally simulate alternate placements for the virtual appliances and modify the placement of the virtual appliances in order to achieve the desired placements.

The desired placements of the virtual brackets on the virtual teeth can be displayed on the workstation 28 as well as printed on paper that can enable the practitioner by providing a visual guide in physically placing the brackets on the real teeth of the patient.

Presently preferred and alternative embodiments of the invention have been set forth. Variations from the preferred and alternative embodiments may be made without departure from the scope and spirit of this invention.

We claim:

1. A method of facilitating placement of virtual appliances at desired positions on virtual teeth of an orthodontic patient using a workstation having a processing unit, memory having a three-dimensional virtual model of teeth of the patient, and an user interface including a display and software executable by said processing unit, comprising the steps of:

(a) displaying three-dimensional virtual teeth model of a patient in a user selected dentition state of a patient;

(b) selecting a virtual appliance placement reference for placing virtual appliances on said virtual teeth;

(c) placing and displaying a virtual appliance at said appliance placement reference on a plurality of said virtual teeth in said user selected dentition state;

(d) evaluating said virtual appliance placement for each of said plurality of virtual teeth is in a desired position;

(e) when one or more of said virtual appliances are not in said desired position, digitally simulating alternate placements for said virtual appliances and modifying said placement of said virtual appliances in order to achieve the desired placements; and (f) displaying said virtual teeth in said virtual model in the form of a virtual two-dimensional (2D) panorax model with axial inclination for each tooth, enabling said practitioner in modifying said placement of said virtual appliances, simulating its overall treatment effectiveness on said patient, and when a desired placement is achieved wrapping said virtual 2D panorax model in three-dimensional (3D) view.

2. The method of claim 1, wherein said user selected dentition state of said patient comprises a malocclusion state.

3. The method of claim 1, wherein said user selected dentition state of said patient comprises a target state.

4. The method of claim 1, wherein said appliance placement reference comprises a bracket height reference and wherein step (b) comprises selecting said bracket height reference in at least one of the following ways: (i) for each of said virtual teeth, (ii) for groups of said virtual teeth, (iii) the same for all of said virtual teeth.

5. The method of claim 1, wherein said appliance placement reference comprises an occlusal plane reference and wherein step (b) comprises selecting said occlusal plane reference, either in whole or in user selected segments.

6. The method of claim 5, wherein said occlusion plane is lower occlusion plane.

7. The method of claim 5, wherein said occlusion plane is upper occlusion plane.

8. The method of claim 5, wherein said occlusion plane is lower occlusion plane and upper plane.

9. The method of claim 5, wherein said occlusion plane is derived from cusp tips.

10. The method of claim 5, wherein said occlusion plane is derived from marginal ridges.

11. The method of claim 5, wherein said occlusion plane is derived arbitrarily.

12. The method of claim 5, wherein said occlusion plane is derived in independent segments.

13. The method of claim 1, wherein said appliance placement reference comprises an arbitrary plane reference and wherein step (b) comprises selecting said arbitrary plane reference, in whole or in user selected segments, in one of the following ways: (i) for lower arch, (ii) for upper arch, (iii) for lower arch and upper arch.

14. The method of claim 1, wherein said virtual teeth comprise virtual teeth on (a) lower jaw, or (b) upper jaw, or (c) lower jaw and upper jaw.

15. The method of claim 1, wherein said virtual appliances comprise virtual brackets prescribed by the practitioner or selected from a library of virtual brackets stored in said workstation's memory or a combination thereof.

16. The method of claim 1, wherein said verifying step (d) includes examining said virtual appliance placement (a) locally for each said virtual tooth, (b) for selected groups of said virtual teeth, and (c) globally for all said virtual teeth.

17. The method of claim 1, wherein said virtual appliances comprise virtual brackets prescribed by the practitioner or selected from a library of virtual brackets stored in said workstation's memory or a combination thereof and wherein said verifying step (d) includes detecting collision (a) between said virtual bracket and said virtual tooth on which said virtual bracket is placed on, and (b) between said one virtual bracket and said another virtual bracket.

18. The method of claim 1, wherein said virtual appliances comprise virtual brackets prescribed by the practitioner or selected from a library of virtual brackets stored in said workstation's memory or a combination thereof and wherein said modifying said placement of said virtual appliances in step (e) further comprises enabling said user in replacing said one or more virtual brackets with those from said library of virtual brackets.

19. The method of claim 1, further comprising the step of automatically measuring and marking said placement of said virtual appliances in relation to the surface of said virtual teeth in 2D and/or 3D.

20. The method of claim 19, wherein said virtual appliances comprise virtual brackets prescribed by the practitioner or selected from a library of virtual brackets stored in said workstation's memory or a combination thereof and wherein said measuring and identifying the placement of said virtual appliances further comprises the step of measuring thickness of the gap between said virtual bracket and said virtual tooth surface for placing an adhesive pad.

21. The method of claim 1, further comprising the step of enabling said user in measuring and marking said placement of said virtual appliances using the graph paper display in 2D and/or 3D.

22. The method of claim 1, wherein said virtual appliances comprise virtual brackets prescribed by the practitioner or selected from a library of virtual brackets stored in said workstation's memory or a combination thereof and wherein said verifying step (d) includes enabling the practitioner in ascertaining that said virtual bracket is placed on the center of said virtual tooth.

23. The method of claim 1, wherein said virtual appliances comprise virtual brackets prescribed by the practitioner or selected from a library of virtual brackets stored in said workstation's memory or a combination thereof and wherein said verifying step (d) further includes enabling the practitioner in viewing said virtual bracket placement using the clipping plane and in ascertaining that said virtual bracket is properly adapted to the surface of said virtual tooth; and said modifying the placement step (e) further comprises moving said virtual bracket to realize proper adaptation of said virtual bracket to the surface of said virtual tooth.

24. The method of claim 1, wherein said virtual appliances comprise virtual brackets prescribed by the practitioner or selected from a library of virtual brackets stored in said workstation's memory or a combination thereof and wherein said verifying step (d) further comprises enabling the practitioner in viewing said virtual bracket placement and in ascertaining that said virtual bracket does not penetrate the surface of said virtual tooth; and said modifying the placement in step (e) includes moving said virtual bracket to realize proper placement to remove any penetration of said virtual bracket from the surface of said virtual tooth.

25. The method of claim 1, wherein said appliance placement reference comprises a bracket height reference and wherein step (b) comprises selecting said bracket height reference in one of the following ways: (i) for each of said virtual teeth, (ii) for groups of said virtual teeth, (iii) the same for all of said virtual teeth and wherein said verifying step (d) further includes enabling the practitioner in viewing said virtual bracket placement in relation to the occlusion plane and ascertaining that said virtual brackets are placed properly; and said modifying the placement in step (e) includes moving said virtual brackets to realize the desired relationship between said virtual brackets and said occlusal plane.

26. The method of claim 25, wherein said occlusal plane is the upper occlusal plane.

27. The method of claim 25, wherein said occlusal plane is the lower occlusal plane.

28. The method of claim 25, wherein said occlusal plane is viewed in arbitrary sections selected by the practitioner.

29. The method of claim 25, further comprising the step of changing the level of said occlusal plane and simulating its overall treatment effectiveness on said patient.

30. The method of claim 25, further comprising the step of changing the angle of said occlusal plane and simulating its overall treatment effectiveness on said patient.

31. The method of claim 25, further comprising the step of changing the curvature of said occlusal plane and simulating its overall treatment effectiveness on said patient.

32. The method of claim 1, wherein said virtual appliances comprise virtual brackets prescribed by the practitioner or selected from a library of virtual brackets stored in said workstation's memory or a combination thereof and wherein said verifying step (d) further comprises enabling said practitioner in checking said placement height, angulation, and torque of said virtual bracket and in step (e) simulating the overall treatment effectiveness of said virtual bracket placement on said patient.

33. The method of claim 1, wherein said virtual appliances comprise virtual brackets prescribed by the practitioner or selected from a library of virtual brackets stored in said workstation's memory or a combination thereof and wherein said verifying step (d) includes enabling said practitioner in ascertaining that the resulting marginal ridges are lined-up; and said modifying said placement step (e) includes moving said virtual bracket or said virtual brackets so that said marginal ridges are aligned.

34. The method of claim 1, wherein said virtual appliances comprise virtual brackets prescribed by the practitioner or selected from a library of virtual brackets stored in said workstation's memory or a combination thereof and wherein said verifying step (d) comprises enabling said practitioner in ascertaining that the cusp tips are in the desired position; and said modifying the placement in step (e) includes the step of moving said virtual bracket or said virtual brackets in order to realize the desired positions of said cusp tips.

35. The method of claim 1, wherein said virtual appliances comprise virtual brackets prescribed by the practitioner or selected from a library of virtual brackets stored in said workstation's memory or a combination thereof and wherein said modifying the placement in step (e) includes enabling the practitioner in placing said virtual bracket such that the reference virtual tooth is blocked from moving and simulating its overall treatment effectiveness on said patient.

36. The method of claim 1, wherein said displaying said virtual appliances on said virtual teeth further comprises the step of enabling said practitioner in hiding said virtual teeth from the view.

37. The method of claim 1, wherein said simulating in step (e) further comprises the step of simulating the effectiveness of the archwire configuration in conjunction with said bracket placement and making adjustments when necessary to realize said desired position of said patient's virtual teeth.

38. The method of claim 37, wherein said archwire comprises a straight archwire.

39. The method of claim 37, wherein said archwire comprises a custom archwire.

40. The method of claim 37, wherein said archwire comprises a hybrid archwire.

41. A method of placing virtual appliances at desired positions on virtual teeth of an orthodontic patient for planning mid-course treatment adjustment using a workstation having a processing unit, memory having a three-dimensional virtual model of teeth of the patient, and an user interface including a display and software executable by said processing unit, comprising the steps of:
  displaying a three-dimensional virtual teeth model of a patient and virtual appliances in their current positions in an intermediate treatment state;
  selecting a virtual appliance placement reference;
  comparing said current virtual appliance placements with the placements recommended by said virtual appliance placement reference;
  when said current position of said virtual appliance in said intermediate treatment state deviates from said appliance placement reference on said virtual tooth, repositioning and displaying said virtual appliance at said appliance placement reference;
  verifying that said virtual appliance placement for each said virtual tooth is in desired position;
  when the virtual appliance is not in said desired position, digitally simulating alternate placements for said virtual appliances and modifying said placement of said virtual appliances in order to achieve the desired placements; and
  displaying said virtual teeth in said virtual model in the form of a virtual two-dimensional (2D) panorax model with axial inclination for each tooth, enabling said practitioner in modifying said placement of said virtual appliances, simulating its overall treatment effectiveness on said patient, and when a desired placement is achieved wrapping said virtual 2D panorax model in three-dimensional (3D) view.

42. The method of claim 41, wherein said appliance placement reference comprises bracket height reference selected in at least one of the following ways: (i) for each of said virtual teeth, (ii) for groups of said virtual teeth, (iii) the same for all of said virtual teeth.

43. The method of claim 41, wherein said appliance placement reference comprises an occlusal plane reference selected either in whole or in user selected segments, in one of the following ways: (i) for lower arch, (ii) for upper arch, (iii) for lower arch and upper arch.

44. The method of claim 41, wherein said appliance placement reference comprises an arbitrary plane reference selected either in whole or in user selected segments, in one of the following ways: (i) for lower arch, (ii) for upper arch, (iii) for lower arch and upper arch.

45. The method of claim 41, wherein said virtual appliances comprise virtual brackets prescribed by said practitioner or selected from a library of virtual brackets stored in said workstation's memory or a combination thereof.

46. An apparatus for facilitating placement of virtual appliances at desired positions on virtual teeth of an an orthodontic patient, comprising:
  a workstation having a processing unit and a display;
  a memory accessible by said workstation storing a virtual three-dimensional model of teeth and/or associated anatomical structures representing the dentition of a patient;
  software executable by said processing unit to access said model and display said model on said display; and
  said software further including navigation tools enabling a user to interactively:
    (a) display said three-dimensional virtual teeth model of a patient in a user selected dentition state of a patient;
    (b) select a virtual appliance placement reference for placing virtual appliances on said virtual teeth;
    (c) place and display a virtual appliance at said appliance placement reference on a plurality of each of said virtual teeth in said user selected dentition state;
    (d) verify and evaluate that said virtual appliance placement for each of said plurality of virtual teeth is in desired position; and
    (e) when one or more of said virtual appliances are not suitably placed, digitally simulate alternate placements for said virtual appliances and modify said placement of said virtual appliances in order to achieve the desired placements;
  wherein the navigation tools further comprise tools enabling the user in displaying the teeth in the virtual model in the form of a two-dimensional (2D) panorax showing axial inclination for each tooth, in modifying the placement of appliances, simulating its overall treatment effectiveness on the patient, and when a desired placement is achieved, in wrapping the virtual 2D model in three-dimensional (3D) view.

47. The apparatus of claim 46, wherein said user selected dentition state of said patient comprises malocclusion state.

48. The apparatus of claim 46, wherein said user selected dentition state of said patient comprises target state.

49. The apparatus of claim 46, wherein said appliance placement reference comprises bracket height reference selected in one of the following ways: (i) for each of said virtual teeth, (ii) for groups of said virtual teeth, (iii) the same for all of said virtual teeth.

50. The apparatus of claim 46, wherein said appliance placement reference comprises arbitrary plane reference selected, either in whole or in user selected segments, in one of the following ways: (i) for lower arch, (ii) for upper arch, (iii) for lower arch and upper arch.

51. The apparatus of claim 50, wherein said arbitrary plane reference comprises occlusal plane reference.

52. The apparatus of claim 46, wherein said navigation tools further enable the user to view and manipulate marginal ridges.

53. The apparatus of claim 46, wherein said navigation tools further enable the user to view and manipulate cusp tips.

54. The apparatus of claim 46, wherein said navigation tools further enable the user to view and select reference tooth or teeth.

55. The apparatus of claim 46, wherein said appliances are brackets.

56. The apparatus of claim 55, wherein said brackets are selected from a library of brackets stored in said workstation's memory.

57. The apparatus of claim 55, wherein said brackets are prescribed by the practitioner.

58. The apparatus of claim 46, wherein said appliances are brackets and wherein said navigation tools further enable the user to detect collision (a) between the bracket and the tooth, (b) between the bracket on one tooth and the bracket on the neighboring tooth on the same arch, and (c) between the bracket on one tooth and the bracket on the neighboring tooth on the opposite arch; and to modify the placement by moving the bracket or the brackets to eliminate collision.

59. The apparatus of claim 46, wherein said appliances are brackets and wherein said navigation tools further enable the user to select a different type of bracket from the bracket library and to replace the current bracket on the particular tooth with the selected bracket and to simulate its overall treatment effectiveness on the patient.

60. The apparatus of claim 46, wherein the navigation tools further comprise tools enabling the user in automatically measuring and to identifying the placement of the appliances in relation to the tooth surface.

61. The apparatus of claim 46, wherein the navigation tools further comprise tools enabling the practitioner in measuring and identifying the placement of the appliances using the graph paper display.

62. The apparatus of claim 61, wherein the measurements are enabled in all three dimensions of space.

63. The apparatus of claim 61, wherein said appliances are brackets and wherein the navigation tools further comprise tools enabling the user in measuring thickness of the gap between the bracket and the tooth surface for placing adhesive pad.

64. The apparatus of claim 46, wherein said appliances are brackets and wherein the navigation tools further comprise tools enabling the user in ascertaining that the bracket is placed on the center of the tooth.

65. The apparatus of claim 46, wherein said appliances are brackets and wherein the navigation tools further comprise tools enabling the user in viewing the bracket placement using the clipping plane and in ascertaining that the bracket is properly adapted to the surface of the tooth; and in moving the bracket to realize proper adaptation of the bracket to the tooth surface.

66. The apparatus of claim 46, wherein said appliances are brackets and wherein the navigation tools further comprise tools enabling the user in viewing the bracket placement and in ascertaining that the bracket does not penetrate the surface of the tooth; and in moving the bracket to realize proper placement to remove any penetration of the bracket from the tooth surface.

67. The apparatus of claim 46, wherein said appliances are brackets and wherein the navigation tools further comprise tools enabling the user in viewing the bracket placement in relation to the occlusion plane and in ascertaining that the brackets are placed properly; and in moving the brackets to realize the desired relationship between the brackets and the occlusal plane.

68. The apparatus of claim 46, wherein said appliances are brackets and wherein the navigation tools further comprise tools enabling the user in checking the placement height, angulation, and torque of the bracket and in simulating its overall treatment effectiveness on the patient.

69. The apparatus of claim 46, wherein said appliances are brackets and wherein the navigation tools further comprise tools enabling the user in ascertaining that the resulting marginal ridges are lined-up; and in moving the bracket or the brackets for aligning the marginal ridges.

70. The apparatus of claim 46, wherein said appliances are brackets and wherein the navigation tools further comprise tools enabling the user in ascertaining that the cusp tips are in the desired position; and in moving the bracket or the brackets for realizing the desired cusp tips positions.

71. The apparatus of claim 46, wherein said appliances are brackets and wherein the navigation tools further comprise tools enabling the user in placing the bracket such that the reference tooth is blocked from displacement and in simulating its overall treatment effectiveness on the patient.

72. The apparatus of claim 46, wherein the navigation tools further comprise tools enabling the user in displaying bounding boxes around the teeth for aiding in assessing teeth movement.

73. The apparatus of claim 46, wherein the navigation tools further comprise special visualization tools enabling the user in selecting, visualizing and modifying said patient's axial inclinations of crowns and roots of said patient's dentition in 2D and 3D.

* * * * *